US007608425B2

(12) United States Patent
Goldenberg et al.

(10) Patent No.: US 7,608,425 B2
(45) **Date of Patent: *Oct. 27, 2009**

(54) METHODS FOR PROTEIN EXPRESSION IN MAMMALIAN CELLS IN SERUM-FREE MEDIUM

(75) Inventors: David M. Goldenberg, Mendham, NJ (US); Chien-Hsing Chang, Downingtown, PA (US); Edward A. Rossi, Nutley, NJ (US); Diane Nordstrom, Rockaway, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/877,728

(22) Filed: Oct. 24, 2007

(65) Prior Publication Data

US 2009/0111143 A1 Apr. 30, 2009

Related U.S. Application Data

(63) Continuation-in-part of application No. 11/487,215, filed on Jul. 14, 2006, now Pat. No. 7,537,930, which is a continuation-in-part of application No. 11/187,863, filed on Jul. 25, 2005, now Pat. No. 7,531,327.

(60) Provisional application No. 60/590,349, filed on Jul. 23, 2004.

(51) Int. Cl.
*C12P 21/06* (2006.01)
*C12N 5/00* (2006.01)
*C12N 15/00* (2006.01)

(52) U.S. Cl. ....................... 435/69.1; 435/455; 435/325

(58) Field of Classification Search ....................... None
See application file for complete search history.

(56) References Cited

U.S. PATENT DOCUMENTS

| | | | | |
|---|---|---|---|---|
| 6,586,206 | B1 | 7/2003 | Dixit et al. | |
| 6,635,448 | B2 | 10/2003 | Bucciarelli et al. | |
| 6,964,199 | B2 | 11/2005 | Lee et al. | |
| 7,531,327 | B2 | 5/2009 | Goldenberg et al. | |
| 2003/0064510 | A1 | 4/2003 | Reff et al. | |
| 2003/0069201 | A1 | 4/2003 | Reed | |
| 2003/0219871 | A1 | 11/2003 | Enenkel et al. | |
| 2007/0015250 | A1 | 1/2007 | Goldenberg et al. | |
| 2007/0092947 | A1* | 4/2007 | Goldenberg et al. | 435/69.2 |

FOREIGN PATENT DOCUMENTS

| | | |
|---|---|---|
| WO | 02/16590 | 2/2002 |
| WO | 02/40665 | 5/2002 |
| WO | 03/040374 | 5/2003 |
| WO | 03/083093 | 10/2003 |
| WO | 2007/015848 | 2/2007 |

OTHER PUBLICATIONS

Arden et al. "Cell engineering blocks stress and improves biotherapeutic production", Bioprocessing Journal, 3:23-28 (2004).
Brenner et al. "Increased p16 expression with first senescence arrest in human mammary epithelial cells and extended growth capacity with p16 inactivation", Oncogene 17:199-205, 1998.
Chang et al. "Effects of p21Waf1/Cip1/Sdi1 on cellular gene expression: Implications for carcinogenesis, senescence, and age-related diseases", Proc Natl Acad Sci USA 97, 4291-6, 2000.
Deng et al. "Mono- and multisite phosphorylation enhances Bcl2's antiapoptotic function and inhibition of cell cycle entry functions", PNAS (101) 153-158, 2004.
Deng et al. "Bcl2 retards G1/S cell cycle transition by regulating intracellular ROS" Blood, vol. 102, No. 9, pp. 3179-3185, 2003.
Finzer et al. "The role of human papillomavirus oncoproteins E6 and E7 in apoptosis", Cancer Lett 188, 15-24, 2002.
Geisse et al. "Eukaryotic Expression Systems: A Comparison" Protein Expression and Purification 8:271-282 (1996).
Ghezzi and Brines "Erythropoietin as an antiapoptotic, tissue-protective cytokine", Cell Death and Differentiation 11 (suppl. 1), s37-s44, Jul. 2004.
Gillies et al. "High-level expression of chimeric antibodies using adapted cDNA variable region cassettes", J. Immunol. Methods 125:191 (1989).
Goldstein and Singal "Senescence of Cultured Human Fibroblasts: Mitotic Versus Metabolic Time", Exp Cell Res 88, 359-64, 1974.
Javelaud et al. "Induction of p21Waf1/Cip1 by TNFa requires NF-kB activity and antagonizes apoptosis in Ewing tumor cells", Oncogene 19, 61-8, 2000.
Lee et al. "Human papilloma virus type 16 E7 genes protect astrocytes against apoptotic and necrotic death induced by hydrogen peroxide", Yonsei Med J 42, 471-9, 2001.
Lee et al. "Development of Apoptosis-Resistant Dihydrofolate Reductase-Deficient Chinese Hamster Ovary Cell Line", Biotechnology & Bioengineering 82:872-76, 2003.
Lotem et al. "Regulation by bcl-2, c-myc, and p53 of Susceptibility to Induction of Apoptosis by Heat Shock and Cancer Chemotherapy Compounds in Differentiation-competent and -defective Myeloid Leukemic Cells", Cell Growth & Differentiation, 4:41-47, 1993.

(Continued)

*Primary Examiner*—Ilia Ouspenski
(74) *Attorney, Agent, or Firm*—Richard A. Nakashima

(57) ABSTRACT

Disclosed are compositions and methods for increasing the longevity of a cell culture and permitting the increased production of proteins, preferably recombinant proteins, such as antibodies, peptides, enzymes, growth factors, interleukins, interferons, hormones, and vaccines. Cells transfected with an apoptosis-inhibiting gene or vector, such as a triple mutant Bcl-2 gene, can survive longer in culture, resulting in extension of the state and yield of protein biosynthesis. Such transfected cells exhibit maximal cell densities that equal or exceed the maximal density achieved by the parent cell lines. Transfected cells can also be pre-adapted for growth in serum-free medium, greatly decreasing the time required to obtain protein production in serum-free medium. In certain methods, the pre-adapted cells can be used for protein production following transfection under serum-free conditions. In preferred embodiments, the cells of use are SpESF or SpESF-X cells.

13 Claims, 20 Drawing Sheets

OTHER PUBLICATIONS

Schwartz et al. "In vitro Meylopoiesis Stimulated by Rapid Medium Exchange and Supplementation with Hematopoietic Growth Factors", Blood 78(12):3155-61, 1991 (Abstract only).

Suzuki et al. "Establishing Apoptosis Resistant Cell Lines for Improving Protein Productivity of Cell Culture" Cytotechnology 23:55-59, 1997.

Romanos et al. "Production of a phosphorylated GST:HPV-6 E7 fusion protein using a yeast expression vector and glutathione S-transferase fusions", Gene, vol. 152, No. 1, pp. 137-138, 1995.

Tey et al. "Influence of Bcl-2 on cell death during cultivation of a Chinese Hamster Ovary cell line expressing a chimeric antibody", Biotechnol. Bioeng. 68: 31-43, 2000.

Vaux et al. "BcI-2 gene promotes haemopoietic cell survival and cooperates with c-myc to immortalize pre-B cells", Nature 335, 440-2, 1988.

Yang et al. "Inhibitors Directed towards Caspase-1 and -3 Are Less Effective than Pan Caspase Inhibition in Preventing Renal Proximal Tubular Cell Apoptosis", Nephron Experimental Nephrology 2004;96:e39-e51.

* cited by examiner

BCL2 Fluorescence
0
100
200
300
400
500
600
700
800
mean
median
SP2/0
Raji
Daudi
SP/EEE #87-29
SP/EEE #7-16

A

B

Viability
SpESF
SpEEE
Sp2/0
% Viability
110
100
90
80
70
60
50
40
30
20
10
0
0
50
100
150
200
250
Hours

Stability of Bcl-2-EEE transgene over time in the presence and absence of zeocin

Guava Express Analysis of Bcl-2 Expression

SEQUENCE LISTING

```
<160> NUMBER OF SEQ ID NOS: 11

<210> SEQ ID NO 1
<211> LENGTH: 9780
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 1

ttccataggc tccgcccccc tgacgagcat cacaaaaatc gacgctcaag tcagaggtgg     60

cgaaacccga caggactata aagataccag gcgtttcccc ctggaagctc cctcgtgcgc    120

tctcctgttc cgaccctgcc gcttaccgga tacctgtccg cctttctccc ttcgggaagc    180

gtggcgcttt ctcatagctc acgctgtagg tatctcagtt cggtgtaggt cgttcgctcc    240

aagctgggct gtgtgcacga accccccgtt cagcccgacc gctgcgcctt atccggtaac    300

tatcgtcttg agtccaaccc ggtaagacac gacttatcgc cactggcagc agccactggt    360

aacaggatta gcagagcgag gtatgtaggc ggtgctacag agttcttgaa gtggtggcct    420

aactacggct acactagaag gacagtattt ggtatctgcg ctctgctgaa gccagttacc    480

ttcggaaaaa gagttggtag ctcttgatcc ggcaaacaaa ccaccgctgg tagcggtggt    540
```

-continued

```
tttttgttt gcaagcagca gattacgcgc agaaaaaaag gatctcaaga agatcctttg    600
atcttttcta cggggtctga cgctcagtgg aacgaaaact cacgttaagg gattttggtc    660
atgagattat caaaaaggat cttcacctag atccttttaa attaaaaatg aagttttaaa    720
tcaatctaaa gtatatatga gtaaacttgg tctgacagtt accaatgctt aatcagtgag    780
gcacctatct cagcgatctg tctatttcgt tcatccatag ttgcctgact ccccgtcgtg    840
tagataacta cgatacggga gggcttacca tctggcccca gtgctgcaat gataccgcga    900
gacccacgct caccggctcc agatttatca gcaataaacc agccagccgg aagggccgag    960
cgcagaagtg gtcctgcaac tttatccgcc tccatccagt ctattaattg ttgccgggaa   1020
gctagagtaa gtagttcgcc agttaatagt ttgcgcaacg ttgttgccat tgctgcaggc   1080
atcgtggtgt cacgctcgtc gtttggtatg gcttcattca gctccggttc ccaacgatca   1140
aggcgagtta catgatcccc catgttgtgc aaaaaagcgg ttagctcctt cggtcctccg   1200
atcgttgtca gaagtaagtt ggccgcagtg ttatcactca tggttatggc agcactgcat   1260
aattctctta ctgtcatgcc atccgtaaga tgcttttctg tgactggtga gtactcaacc   1320
aagtcattct gagaatagtg tatgcggcga ccgagttgct cttgcccggc gtcaacacgg   1380
gataataccg cgccacatag cagaacttta aaagtgctca tcattggaaa acgttcttcg   1440
gggcgaaaac tctcaaggat cttaccgctg ttgagatcca gttcgatgta acccactcgt   1500
gcacccaact gatcttcagc atcttttact ttcaccagcg tttctgggtg agcaaaaaca   1560
ggaaggcaaa atgccgcaaa aaagggaata agggcgacac ggaaatgttg aatactcata   1620
ctcttccttt ttcaatatta ttgaagcatt tatcagggtt attgtctcat gagcggatac   1680
atatttgaat gtatttagaa aaataaacaa ataggggttc cgcgcacatt tccccgaaaa   1740
ggccacctga cgtctaagaa accattatta tcatgacatt aacctataaa aataggcgta   1800
tcacgaggcc ctttcgtctt caagaattcc gatccagaca tgataagata cattgatgag   1860
tttggacaaa ccacaactag aatgcagtga aaaaaatgct ttatttgtga aatttgtgat   1920
gctattgctt tatttgtaac cattataagc tgcaataaac aagttaacaa caacaattgc   1980
attcatttta tgtttcaggt tcagggggag gtgtgggagg ttttttaaag caagtaaaac   2040
ctctacaaat gtggtatggc tgattatgat ctaaagccag caaaagtccc atggtcttat   2100
aaaaatgcat agctttagga ggggagcaga gaacttgaaa gcatcttcct gttagtcttt   2160
cttctcgtag acttcaaact tatacttgat gccttttttcc tcctggacct cagagaggac   2220
gcctgggtat tctgggagaa gtttatattt ccccaaatca atttctggga aaaacgtgtc   2280
actttcaaat tcctgcatga tccttgtcac aaagagtctg aggtggcctg gttgattcat   2340
ggcttcctgg taaacagaac tgcctccgac tatccaaacc atgtctactt tacttgccaa   2400
ttccggttgt tcaataagtc ttaaggcatc atccaaactt ttggcaagaa aatgagctcc   2460
tcgtggtggt tctttgagtt ctctactgag aactatatta attctgtcct ttaaaggtcg   2520
attcttctca ggaatggaga accaggtttt cctacccata atcaccagat tctgtttacc   2580
ttccactgaa gaggttgtgg tcattctttg gaagtacttg aactcgttcc tgagcggagg   2640
ccagggtcgg tctccgttct tgccaatccc catattttgg gacacggcga cgatgcagtt   2700
caatggtcga accatgaggg caccaagcta gctttttgca aaagcctagg cctccaaaaa   2760
agcctcctca ctacttctgg aatagctcag aggccgaggc ggcctcggcc tctgcataaa   2820
taaaaaaaat tagtcagcca tggggcggag aatgggcgga actgggcgga gttaggggcg   2880
```

-continued

```
ggatgggcgg agttaggggc gggactatgg ttgctgacta attgagatgc atgctttgca   2940
tacttctgcc tgctggggag cctggggact ttccacacct ggttgctgac taattgagat   3000
gcatgctttg catacttctg cctgctgggg agcctgggga ctttccacac cctaactgac   3060
acacattcca cagtcgacta gaatatggat agtgggtgtt tatgactctg gataagcctg   3120
aacaattgat gattaatgcc cctgagctct gttcttagta acatgtgaac atttacttgt   3180
gtcagtgtag tagatttcac atgacatctt ataataaacc tgtaaatgaa agtaatttgc   3240
attactagcc cagcccagcc catactaaga gttatattat gtctgtctca cagcctgctg   3300
ctgaccaata ttgaaaagaa tagaccttcg actggcagga agcaggtcat gtggcaaggc   3360
tatttgggga agggaaaata aaaccactag gtaaacttgt agctgtggtt tgaagaagtg   3420
gttttgaaac actctgtcca gccccaccaa accgaaagtc caggctgagc aaaacaccac   3480
ctgggtaatt tgcatttcta aaataagttg aggattcagc cgaaactgga gaggtcctct   3540
tttaacttat tgagttcaac cttttaattt tagcttgagt agttctagtt tccccaaact   3600
taagtttatc gacttctaaa atgtatttag aatttcgacc aattctcatg tttgacagct   3660
tatcatcgct gcactccgcc cgaaaagtgc gctcggctct gccaaggacg cggggcgcgt   3720
gactatgcgt gggctggagc aaccgcctgc tgggtgcaaa ccctttgcgc ccggactcgt   3780
ccaacgacta taaagagggc aggctgtcct ctaagcgtca ccacgacttc aacgtcctga   3840
gtaccttctc ctcacttact ccgtagctcc agcttcacca gatccctcga ctctagaggc   3900
cttaagggcc ttactgagca cacaggacct caccatggga tggagctgta tcatcctctt   3960
cttggtagca acagctacag gtaaggggct cacagtagca ggcttgaggt ctggacatat   4020
atatgggtga caatgacatc cactttgcct ttctctccac aggtgtccac tccgacatcc   4080
agctgaccca gagcccaagc agcctgagcg ccagcgtggg tgacagagtg accatcacct   4140
gtaaggccag tcaggatgtg ggtacttctg tagcctggta ccagcagaag ccaggtaagg   4200
ctccaaagct gctgatctac tggacatcca cccggcacac tggtgtgcca agcagattca   4260
gcggtagcgg tagcggtacc gacttcacct tcaccatcag cagcctccag ccagaggaca   4320
tcgccaccta ctactgccag caatatagcc tctatcggtc gttcggccaa gggaccaagg   4380
tggaaatcaa acgtgagtag aatttaaact ttgcttcctc agttggatcc cgcaattcta   4440
aactctgagg gggtcggatg acgtggccat tctttgccta aagcattgag tttactgcaa   4500
ggtcagaaaa gcatgcaaag ccctcagaat ggctgcaaag agctccaaca aaacaattta   4560
gaactttatt aaggaatagg gggaagctag gaagaaactc aaaacatcaa gattttaaat   4620
acgcttcttg gtctccttgc tataattatc tgggataagc atgctgtttt ctgtctgtcc   4680
ctaacatgcc ctgtgattat ccgcaaacaa cacacccaag ggcagaactt tgttacttaa   4740
acaccatcct gtttgcttct ttcctcagga actgtggctg caccatctgt cttcatcttc   4800
ccgccatctg atgagcagtt gaaatctgga actgcctctg ttgtgtgcct gctgaataac   4860
ttctatccca gagaggccaa agtacagtgg aaggtggata acgccctcca atcgggtaac   4920
tcccaggaga gtgtcacaga gcaggacagc aaggacagca cctacagcct cagcagcacc   4980
ctgacgctga gcaaagcaga ctacgagaaa cacaaagtct acgcctgcga agtcacccat   5040
cagggcctga gctcgcccgt cacaaagagc ttcaacaggg gagagtgtta gagggagaag   5100
tgcccccacc tgctcctcag ttccagcctg accccctccc atcctttggc ctctgaccct   5160
ttttccacag ggacctaccc cctattgcgg tcctccagct catctttcac ctcacccccc   5220
tcctcctcct tggctttaat tatgctaatg ttggaggaga atgaataaat aaagtgaatc   5280
```

-continued tttgcacctg tggtttctct ctttcctcat ttaataatta ttatctgttg ttttaccaac 5340
tactcaattt ctcttataag ggactaaata tgtagtcatc ctaaggcgca taaccattta 5400
taaaaatcat ccttcattct attttaccct atcatcctct gcaagacagt cctccctcaa 5460
acccacaagc cttctgtcct cacagtcccc tgggccatgg taggagagac ttgcttcctt 5520
gttttcccct cctcagcaag ccctcatagt cctttttaag ggtgacaggt cttacagtca 5580
tatatccttt gattcaattc cctgagaatc aaccaaagca aatttttcaa aagaagaaac 5640
ctgctataaa gagaatcatt cattgcaaca tgatataaaa taacaacaca ataaaagcaa 5700
ttaaataaac aaacaatagg gaaatgttta agttcatcat ggtacttaga cttaatggaa 5760
tgtcatgcct tatttacatt tttaaacagg tactgaggga ctcctgtctg ccaagggccg 5820
tattgagtac tttccacaac ctaatttaat ccacactata ctgtgagatt aaaaacattc 5880
attaaaatgt tgcaaaggtt ctataaagct gagagacaaa tatattctat aactcagcaa 5940
ttcccacttc taggggttcg actggcagga agcaggtcat gtggcaaggc tatttgggga 6000
agggaaaata aaaccactag gtaaacttgt agctgtggtt tgaagaagtg gttttgaaac 6060
actctgtcca gccccaccaa accgaaagtc caggctgagc aaaacaccac ctgggtaatt 6120
tgcatttcta aaataagttg aggattcagc cgaaactgga gaggtcctct tttaacttat 6180
tgagttcaac cttttaattt tagcttgagt agttctagtt tccccaaact taagtttatc 6240
gacttctaaa atgtatttag aatttcgacc aattctcatg tttgacagct tatcatcgct 6300
gcactccgcc cgaaaagtgc gctcggctct gccaaggacg cggggcgcgt gactatgcgt 6360
gggctggagc aaccgcctgc tgggtgcaaa ccctttgcgc ccggactcgt ccaacgacta 6420
taaagagggc aggctgtcct ctaagcgtca ccacgacttc aacgtcctga gtaccttctc 6480
ctcacttact ccgtagctcc agcttcacca gatccctcga gcacacagga cctcaccatg 6540
ggatggagct gtatcatcct cttcttggta gcaacagcta caggtaaggg gctcacagta 6600
gcaggcttga ggtctggaca tatatatggg tgacaatgac atccactttg cctttctctc 6660
cacaggtgtc cactcccagg tccaactgca ggagagcggt ggaggtgttg tgcaacctgg 6720
ccggtccctg cgcctgtcct gctccgcatc tggcttcgat ttcaccacat attggatgag 6780
ttgggtgcga caggcacctg gaaaaggtct tgagtggatt ggagaaattc atccagatag 6840
cagtacgatt aactatgcgc cgtcgctaaa agatagattt acaatatcgc gagacaacgc 6900
caagaacaca ttgttcctgc aaatggacag cctgagaccc gaagacaccg gggtctattt 6960
ttgtgcaagc ctttacttcg gcttcccctg gtttgcttat tggggccaag ggaccccggt 7020
caccgtctcc tcaggtgagt ccttacaacc tctctcttct attcagctta aatagatttt 7080
actgcatttg ttggggggga aatgtgtgta tctgaatttc aggtcatgaa ggactaggga 7140
caccttggga gtcagaaagg gtcattggga gccccaagct ttctggggca ggccaggcct 7200
gaccttggct ttggggcagg gagggggcta aggtgaggca ggtggcgcca gccaggtgca 7260
cacccaatgc ccatgagccc agacactgga cgctgaacct cgcggacagt taagaaccca 7320
ggggcctctg cgccctgggc ccagctctgt cccacaccgc ggtcacatgg caccacctct 7380
cttgcagcct ccaccaaggg cccatcggtc ttccccctgg caccctcctc caagagcacc 7440
tctgggggca cagcggccct gggctgcctg gtcaaggact acttccccga accggtgacg 7500
gtgtcgtgga actcaggcgc cctgaccagc ggcgtgcaca ccttcccggc tgtcctacag 7560
tcctcaggac tctactccct cagcagcgtg gtgaccgtgc cctccagcag cttgggcacc 7620

-continued

```
cagacctaca tctgcaacgt gaatcacaag cccagcaaca ccaaggtgga caagagagtt   7680

ggtgagaggc cagcacaggg agggagggtg tctgctggaa gccaggctca gcgctcctgc   7740

ctggacgcat cccggctatg cagccccagt ccagggcagc aaggcaggcc ccgtctgcct   7800

cttcacccgg agcctctgcc cgccccactc atgctcaggg agagggtctt ctggcttttt   7860

cccaggctct gggcaggcac aggctaggtg cccctaaccc aggccctgca cacaaagggg   7920

caggtgctgg gctcagacct gccaagagcc atatccggga ggaccctgcc cctgacctaa   7980

gcccacccca aaggccaaac tctccactcc ctcagctcgg acaccttctc tcctcccaga   8040

ttccagtaac tcccaatctt ctctctgcag agcccaaatc ttgtgacaaa actcacacat   8100

gcccaccgtg cccaggtaag ccagcccagg cctcgccctc cagctcaagg cgggacaggt   8160

gccctagagt agcctgcatc cagggacagg ccccagccgg gtgctgacac gtccacctcc   8220

atctcttcct cagcacctga actcctgggg ggaccgtcag tcttcctctt ccccccaaaa   8280

cccaaggaca ccctcatgat ctcccggacc cctgaggtca catgcgtggt ggtggacgtg   8340

agccacgaag accctgaggt caagttcaac tggtacgtgg acggcgtgga ggtgcataat   8400

gccaagacaa agccgcggga ggagcagtac aacagcacgt accgggtggt cagcgtcctc   8460

accgtcctgc accaggactg gctgaatggc aaggagtaca agtgcaaggt ctccaacaaa   8520

gccctcccag cccccatcga gaaaaccatc tccaaagcca aaggtgggac ccgtggggtg   8580

cgagggccac atggacagag gccggctcgg cccaccctct gccctgagag tgaccgctgt   8640

accaacctct gtcctacagg gcagccccga gaaccacagg tgtacaccct gcccccatcc   8700

cgggaggaga tgaccaagaa ccaggtcagc ctgacctgcc tggtcaaagg cttctatccc   8760

agcgacatcg ccgtggagtg ggagagcaat gggcagccgg agaacaacta caagaccacg   8820

cctcccgtgc tggactccga cggctccttc ttcctctata gcaagctcac cgtggacaag   8880

agcaggtggc agcaggggaa cgtcttctca tgctccgtga tgcatgaggc tctgcacaac   8940

cactacacgc agaagagcct ctccctgtct ccgggtaaat gagtgcgacg gccggcaagc   9000

ccccgctccc cgggctctcg cggtcgcacg aggatgcttg gcacgtaccc cgtctacata   9060

cttcccaggc acccagcatg gaaataaagc acccaccact gccctgggcc cctgcgagac   9120

tgtgatggtt ctttccacgg gtcaggccga gtctgaggcc tgagtggcat gagggaggca   9180

gagcgggtcc cactgtcccc acactggccc aggctgtgca ggtgtgcctg ggccgcctag   9240

ggtggggctc agccaggggc tgccctcggc agggtggggg atttgccagc gtggccctcc   9300

ctccagcagc agctgcctcg cgcgtttcgg tgatgacggt gaaaacctct gacacatgca   9360

gctcccggag acggtcacag cttgtctgta agcggatgcc gggagcagac aagcccgtca   9420

gggcgcgtca gcgggtgttg gcgggtgtcg gggcgcagcc atgacccagt cacgtagcga   9480

tagcggagtg tatactggct taactatgcg gcatcagagc agattgtact gagagtgcac   9540

catatgcggt gtgaaatacc gcacagatgc gtaaggagaa aataccgcat caggcgctct   9600

tccgcttcct cgctcactga ctcgctgcgc tcggtcgttc ggctgcggcg agcggtatca   9660

gctcactcaa aggcggtaat acggttatcc acagaatcag gggataacgc aggaaagaac   9720

atgtgagcaa aggccagcaa aaggccagg aaccgtaaaa aggccgcgtt gctggcgttt   9780
```

<210> SEQ ID NO 2
<211> LENGTH: 420
<212> TYPE: DNA
<213> ORGANISM: Artificial Sequence
<220> FEATURE:
<223> OTHER INFORMATION: Description of Artificial Sequence: Synthetic -continued nucleotide sequence

<400> SEQUENCE: 2

```
caatggtcga accatgaggg caccaagcta gctttttgca aaagcctagg cctccaaaaa     60

agcctcctca ctacttctgg aatagctcag aggccgaggc ggcctcggcc tctgcataaa    120

taaaaaaaat tagtcagcca tggggcggag aatgggcgga actgggcgga gttaggggcg    180

ggatgggcgg agttaggggc gggactatgg ttgctgacta attgagatgc atgctttgca    240

tacttctgcc tgctggggag cctggggact ttccacacct ggttgctgac taattgagat    300

gcatgctttg catacttctg cctgctgggg agcctgggga ctttccacac cctaactgac    360

acacattcca cagtcgacta gaatatggat agtgggtgtt tatgactctg gataagcctg    420
```

<210> SEQ ID NO 3
<211> LENGTH: 720
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 3

```
atggcgcacg ctgggagaac ggggtacgat aaccgggaga tagtgatgaa gtacatccat     60

tataagctgt cgcagagggg ctacgagtgg gatgcgggag atgtgggcgc cgcgcccccg    120

ggggccgccc ccgcaccggg catcttctcc tcccagcccg ggcacacgcc ccatccagcc    180

gcatcccgcg acccggtcgc cagagaagaa ccgctgcaga ctccggctgc tcctggagca    240

gctgcaggac ctgcgctcga accggtgcca cctgtggtcc acctgaccct ccgccaggcc    300

ggcgacgact tctcccgccg ctaccgccgc gacttcgccg agatgtccag ccagctgcac    360

ctgacgccct tcaccgcgcg gggacgcttt gccacggtgg tggaggagct cttcagggac    420

ggggtgaact gggggaggat tgtggccttc tttgagttcg gtggggtcat gtgtgtggag    480

agcgtcaacc gggagatgtc gcccctggtg gacaacatcg ccctgtggat gactgagtac    540

ctgaaccggc acctgcacac ctggatccag gataacggag gctgggatgc ctttgtggaa    600

ctgtacggcc ccagcatgcg gcctctgttt gatttctcct ggctgtctct gaagactctg    660

ctcagtttgg ccctggtggg agcttgcatc accctgggtg cctatctggg ccacaagtga    720
```

<210> SEQ ID NO 4
<211> LENGTH: 239
<212> TYPE: PRT
<213> ORGANISM: Artificial Sequence
<220> FEATURE:
<223> OTHER INFORMATION: Description of Artificial Sequence: Synthetic protein

<400> SEQUENCE: 4

```
Met Ala His Ala Gly Arg Thr Gly Tyr Asp Asn Arg Glu Ile Val Met
  1               5                  10                  15

Lys Tyr Ile His Tyr Lys Leu Ser Gln Arg Gly Tyr Glu Trp Asp Ala
             20                  25                  30

Gly Asp Val Gly Ala Ala Pro Pro Gly Ala Ala Pro Ala Pro Gly Ile
         35                  40                  45

Phe Ser Ser Gln Pro Gly His Thr Pro His Pro Ala Ala Ser Arg Asp
     50                  55                  60

Pro Val Ala Arg Glu Glu Pro Leu Gln Thr Pro Ala Ala Pro Gly Ala
 65                  70                  75                  80
```

-continued

```
Ala Ala Gly Pro Ala Leu Glu Pro Val Pro Pro Val Val His Leu Thr
                 85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235
```

<210> SEQ ID NO 5
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5

```
ggacccggtc gccagagaag aaccgctgca gactccggct gctcctggag cagctgcagg     60

acctgcgctc gaaccggtgc                                                 80
```

<210> SEQ ID NO 6
<211> LENGTH: 80
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6

```
cgccggcctg gcggagggtc aggtggacca caggtggcac cggttcgagc gcaggtcctg     60

cagctgctcc aggagcagcc                                                 80
```

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

```
Asp Glu Val Asp
  1
```

<210> SEQ ID NO 8
<211> LENGTH: 24
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 8

atgtttcagg acccacagga gcga                                           24


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

ttatggtttc tgagaacaga tggg                                           24


<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

tatatggacc cggtcgccag agaag                                          25


<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

ttaatcgccg gcctggcgga gggtc                                          25
```

METHODS FOR PROTEIN EXPRESSION IN MAMMALIAN CELLS IN SERUM-FREE MEDIUM

RELATED APPLICATIONS

The present application is a continuation-in-part of U.S. Patent Application Publ. No. 20070015250, filed Jul. 14, 2006, which was a continuation-in-part of U.S. Patent Application Publ. No. 20060110793, filed Jul. 25, 2005, which claimed the benefit under 35 U.S.C. § 119(e) of provisional U.S. Patent Application Ser. No. 60/590,349, filed Jul. 23, 2004, each of which is incorporated herein by reference in its entirety.

FIELD OF THE INVENTION

Various embodiments of the present invention concern methods and compositions for increasing longevity and/or protein yield from a cell line. In particular embodiments, the cell line may be a hybridoma cell line that produces antibodies, antibody fragments or other therapeutic proteins. In more particular embodiments, the methods may comprise transfecting a cell line with one or more genes, such as genes encoding E6, E7 and/or Bcl-2 or related proteins. Such proteins are not limited to their native sequence, but may include one or more substituted amino acids. Other embodiments concern mammalian cell lines that are capable of growth, transfection and protein production in serum-free medium. Such cell lines may be used in methods of protein production, by transfecting the cell line with an expression vector that expresses a heterologous protein. In preferred embodiments, the cell line may be transfected in serum-free medium, providing considerable time savings in avoiding having to adapt the transfected cell line for serum-free growth and protein production. A more preferred embodiment concerns the SpESF cell line, produced by transfecting the Sp2/0 cell line with a triple mutant Bcl-2 gene (T69E, S70E, S87E) followed by adaptation for growth in serum-free medium to produce SpESF. The SpESF cell line may be grown, transfected and produces proteins in serum-free medium. SpESF may be further adapted by exposure to stressful growth conditions to produce highly robust, serum-free cell lines such as SpESF-X.

BACKGROUND OF THE INVENTION

In 2006, biopharmaceuticals, including monoclonal antibodies (mAbs) and other recombinant proteins, accounted for nearly half of all drugs in the development phase and a quarter of drugs in preclinical and clinical trials (Walsh, 2006, Nat Biotechnol 24:769-776). As the demand for biopharmaceuticals continues to increase, there is a commensurate need for better bioproduction vehicles. Although non-mammalian production systems, such as cultured *Escherichia coli*, yeast, plant and insect cell lines, often result in high yields, cultured mammalian host cell lines are preferred for production of many humanized proteins that require post-translational modifications to preserve their bioactivity.

Culturing cells in vitro, especially in large bioreactors, has been the basis of the production of numerous biotechnology products, and involves the elaboration by these cells of protein products into the support medium, from which these products are isolated and further processed prior to use clinically. The quantity of protein production over time from the cells growing in culture depends on a number of factors, such as, for example, cell density, cell cycle phase, cellular biosynthesis rates of the proteins, condition of the medium used to support cell viability and growth, and the longevity of the cells in culture (i.e., how long before they succumb to programmed cell death, or apoptosis). Various methods of improving the viability and lifespan of the cells in culture have been developed, together with methods of increasing productivity of a desired protein by, for example, controlling nutrients, cell density, oxygen and carbon dioxide content, lactate dehydrogenase, pH, osmolarity, catabolites, etc. For example, increasing cell density can make the process more productive, but can also reduce the lifespan of the cells in culture. Therefore, it may be desirous to reduce the rate of proliferation of such cells in culture when the maximal density is achieved, so as to maintain the cell population in its most productive state as long as possible. This results in increasing or extending the bioreactor cycle at its production peak, elaborating the desired protein products for a longer period, and this results in a higher yield from the bioreactor cycle.

Many different approaches have been pursued to increase the bioreactor cycle time, such as adjusting the medium supporting cell proliferation, addition of certain growth-promoting factors, as well as inhibiting cell proliferation without affecting protein synthesis. One particular approach aims to increase the lifespan of cultured cells via controlling the cell cycle by use of genes or antisense oligonucleotides to affect cell cycle targets, whereby a cell is induced into a pseudo-senescence stage by transfecting, transforming, or infecting with a vector that prevents cell cycle progression and induces a so-called pseudo-senescent state that blocks further cell division and expands the protein synthesis capacity of the cells in culture; in other words, the pseudo-senescent state can be induced by transfecting the cells with a vector expressing a cell cycle inhibitor (Bucciarelli et al., U.S. Patent Appl. 2002/0160450 A1; WO 02/16590 A2). The latter method, by inhibiting cell duplication, seeks to force cells into a state that may have prolonged cell culture lifetimes, as described by Goldstein and Singal (Exp Cell Res 88, 359-64, 1974; Brenner et al., Oncogene 17:199-205, 1998), and may be resistant to apoptosis (Chang et al., Proc Natl Acad Sci USA 97, 4291-6, 2000; Javeland et al., Oncogene 19, 61-8, 2000).

Still another approach involves establishing primary, diploid human cells or their derivatives with unlimited proliferation following transfection with the adenovirus E1 genes. The new cell lines, one of which is PER.C6 (ECACC deposit number 96022940), which expresses functional Ad5 E1A and E1B gene products, can produce recombinant adenoviruses, as well as other viruses (e.g., influenza, herpes simplex, rotavirus, measles) designed for gene therapy and vaccines, as well as for the production of recombinant therapeutic proteins, such as human growth factors and human antibodies (Vogels et al., WO 02/40665 A2).

Other approaches have focused on the use of caspase inhibitors for preventing or delaying apoptosis in cells. See, for example, U.S. Pat. No. 6,586,206. Still other approaches have tried to use apoptosis inhibitors such as members of the Bcl-2 family for preventing or delaying apoptosis in cells. See Arden et al., Bioprocessing Journal, 3:23-28 (2004). These approaches have yielded unpredictable results. For example, in one study, expression of Bcl-2 increased cell viability but did not increase protein production. (See Tey et al., Biotechnol. Bioeng. 68:31-43, 2000.) Another example disclosed overexpression of Bcl-2 proteins to delay apoptosis in CHO cells, but Bcl-xL increased protein production whereas Bcl-2 decreased protein production (see WO03/083093). A further example disclosed experiments using expression of Bcl-2 proteins to prolong the survival of Sp2/0-Ag14 (ATCC #

CRL-1581, hereafter referred to as Sp2/0) cells in cultures. However, the cell density of the Bcl-2 expressing clones were 20 to 50% lower than that of their parental cultures, raising concerns for their practical application in biopharmaceutical industry (see WO03/040374; U.S. Pat. No. 6,964,199).

It is apparent, therefore, that improved host cells for high level expression of recombinant proteins and methods for reliably increasing recombinant protein production, in particular the production of antibodies and antibody fragments, multispecific antibodies, fragments and single-chain constructs, peptides, enzymes, growth factors, hormones, interleukins, interferons, and vaccines, in host cells are needed in the art. A need also exists for cell lines that are pre-adapted to grow in serum-free or serum-depleted medium, that can be transfected with expression vectors under serum free conditions and used for protein production without going through a lengthy adaptation period before serum-free growth and protein production.

SUMMARY OF THE INVENTION

The present invention fulfills unresolved needs in the art by providing improved host cells and methods to increase the longevity and/or recombinant protein yields of a cell culture. In some embodiments, the methods involve introducing into cells agents that inhibit senescence or that promote cell survival, e.g., anti-apoptotic agents. The use of such agents preferentially increases the lifespan and viability of cells in culture used for the production of a desired recombinant protein, concomitantly increasing the productivity of such cells in culture, and thereby the optimal yield of the desired protein. Preferably, the apoptosis inhibitors used in the method of the present invention include but are not limited to Bcl-2 and its family members. Alternately, the longevity and recombinant protein yields of a cell clone can be improved by introducing into the cell agents that down-regulate the level of intracellular pro-apoptotic proteins, such as p53 and Rb, or up-regulate intracellular anti-apoptotic proteins, such as Bcl-2.

Preferably, the regulatory agents used in the claimed methods include, but are not limited to, human papillomavirus type 16 (HPV-16) oncoproteins E6 and E7, anti-apoptosis protein Bcl-2 and combinations thereof. Additionally, caspase inhibitors, as described herein, may also contribute to blocking or reducing apoptosis, thus increasing cell survival and increasing the production of recombinant proteins by said cells in culture. A further class of anti-apoptotic agents that can be used in these cultures to enhance production of recombinant proteins includes certain members of the cytokine type I superfamily, such as erythropoietin (EPO). EPO, as a prototype molecule of this class, is a major modifier of apoptosis of multiple cell types, not just erythrocytes, and thus has more general cytoprotective functions, such as in endothelial cells, myocardial cells, tubular epithelial cells of the kidney, skin, and neurons [cf. review by P. Ghezzi and M. Brines, Cell Death and Differentiation 11 (suppl. 1), s37-s44, July 2004]. In alternative embodiments, host cell lines may be transfected with expression vectors comprising EPO and/or EPOR, instead of supplying EPO externally. (See, e.g., Levin et al., FEBS Lett. 427:164-70, 1998.)

In various embodiments, the cell lines that have been transfected with one or more regulatory agents, such as HPV-16, E6, E7 and/or Bcl-2 may be pre-adapted for growth in serum-free medium. Such pre-adapted cell lines, including but not limited to the SpESF cell line (see Examples below), are able to undergo further transfection, under serum-free conditions, with one or more expression vectors, thus allowing expression and protein production under serum-free conditions without extensive time required for adaption to serum-free growth. This surprising result allows protein production under serum free or low serum conditions, providing significant savings on medium cost. At the same time, transfection and protein production under serum-free conditions saves substantial time needed for serum-free adaptation that is required when using standard mammalian cell lines, which are only transfectable under serum-rich conditions and require an additional 6 to 12 months to adapt to serum-free protein production. Certain pre-adapted cell lines, such as SpESF, may be "banked" or stored frozen and then thawed before transfection with an expression vector to produce recombinant proteins. The ability to bank such pre-adapted cell lines provides significant savings in time, cost and efficiency of protein production.

In other embodiments, transfected and pre-adapted cell lines, such as SpESF, may be further adapted by exposure to stressful growth conditions, such as over-growing the cells until viability is reduced to about 50-75%, followed by full recovery. Such stressful conditions favor the growth of highly robust, high productivity cell lines such as the SpESF-X cell line (see Examples below). These robust, high-productivity cell lines can achieve protein production levels that are substantially higher than the parent cell lines.

The claimed cell culture methods incorporating novel combinations of factors including, but not limited to, transfection vectors, screening and selection of cell clones with desired properties, cell culture media, growth conditions, bioreactor configurations, and cell types to create cell culture conditions in which the longevity of the cell culture is increased and/or made optimal and the yield of a desired recombinant protein is increased. These cell culture methods include suspension, perfusion, and fed-batch methods of production. See Tey et al., J. Biotechnol. 79: 147-159 (2000); Zhang et al., J. Chem. Technol. Biotechnol. 79: 171-181 (2004); Zhou et al., Biotechnol. Bioeng. 55: 783-792 (1997).

Unless otherwise defined, all technical and scientific terms used herein have their plain and ordinary meaning. In addition, the contents of all patents and other references cited herein are incorporated by reference in their entirety.

BRIEF DESCRIPTION OF DRAWINGS/FIGURES

FIG. 1. Immunoblot analysis of SP2/0 transgenic clones for Bcl-2-EEE expression. For 40 clones, total protein was resolved by SDS-PAGE under denaturing conditions and transferred to PVDF membranes. Approximately 10K cells were loaded per lane. Blots were probed with anti-hBcl-2 (C-2) for detection of Bcl-2-EEE and anti-β actin for loading control. The three highest-expressing clones (7, 25 and 87) are identified. Lanes representing a transgenic Sp2/0 clone expressing wild-type hBcl-2 are indicated (wt).

FIG. 2. Flow cytometry analysis of Bcl-2-EEE expression in selected sub-clones. Permeabilized cells were stained with anti-hBcl-2-PE and analyzed by flow cytometry using a Guava PCA and Guava Express software.

FIG. 3. Comparison of the level of Bcl-2 expression of subclones #87-29 and #7-16 with, Raji, Daudi, and Sp2/0 cells. A. Permeabilized cells were stained with anti-hBcl-2-PE and analyzed by flow cytometry using a Guava PCA and Guava Express software. B. Anti-hBcl-2 immunoblot analysis. Total protein was resolved by SDS-PAGE under denaturing conditions and transferred to PVDF membranes. Blots were probed with anti-hBcl-2 (C-2) for detection of Bcl-2-EEE and anti-β actin for loading control. The cell equivalent/lane is indicated. The positions of Bcl-2-EEE and β-actin are indicated with arrows. Sp2/0-Bcl-2(wt) is a transgenic line that over-expresses wild-type hBcl-2 at a high level. C. Immunoblot analysis using a MAb that recognizes both mouse and human Bcl-2.

FIG. 4. Growth (A) and viability (B) curves of the five highest Bcl-2-EEE expressing clones compared to Sp2/0. T25 flasks were seeded at $5\times10^4$ cells/ml in media containing 10% FBS. Viable cell density and viability were measured with a Guava PCA over two weeks.

FIG. 5. Growth and viability curves comparing SpEEE subclones, #87-29 and #7-16, to Sp2/0 in culture media containing (A & B) 10% FBS, (C & D) 1% FBS and (E & F) 0% FBS. Cells were seeded at $2\times10^5$ cells/well in T25 flasks. Viable cell density and viability were measured with a Guava PCA over 12 days.

FIG. 6. Growth curve comparing SpEEE subclones in T-25 flasks over five days of culture. Cells were seeded at $3\times10^5$ cells/ml in serum-free media. Viable cell density was measured with a Guava PCA.

FIG. 7. Growth (A) and viability (B) curves comparing SpESF, Sp2/0 and SpEEE cell lines. T25 flasks were seeded at $1\times10^5$ cells/ml in media containing 10% FBS for SpEEE and Sp2/0 cells or media without FBS for SpESF cells. Viable cell density and viability were measured with a Guava PCA.

FIG. 8. Growth and viability curves comparing SpESF-X subclones #1-8 (A and B) and #9-14 (C and D) cell lines. T25 flasks were seeded at $1\times10^5$ cells/ml in 0% H-SFM. Viable cell density and viability were measured with a Guava PCA.

FIG. 9. Growth (A) and viability (B) curves comparing 5 SpESF-X subclones to parental SpES-X, SpEEE and Sp2/0 cell lines.

FIG. 10. Flow cytometry analysis of Bcl-2-EEE expression in select cell lines maintained in the absence or presence of zeocin. Permeabilized cells were stained with anti-hBcl-2-PE and analyzed by flow cytometry using Guava PCA and Guava Express software.

DETAILED DESCRIPTION OF THE INVENTION

Figure 1:
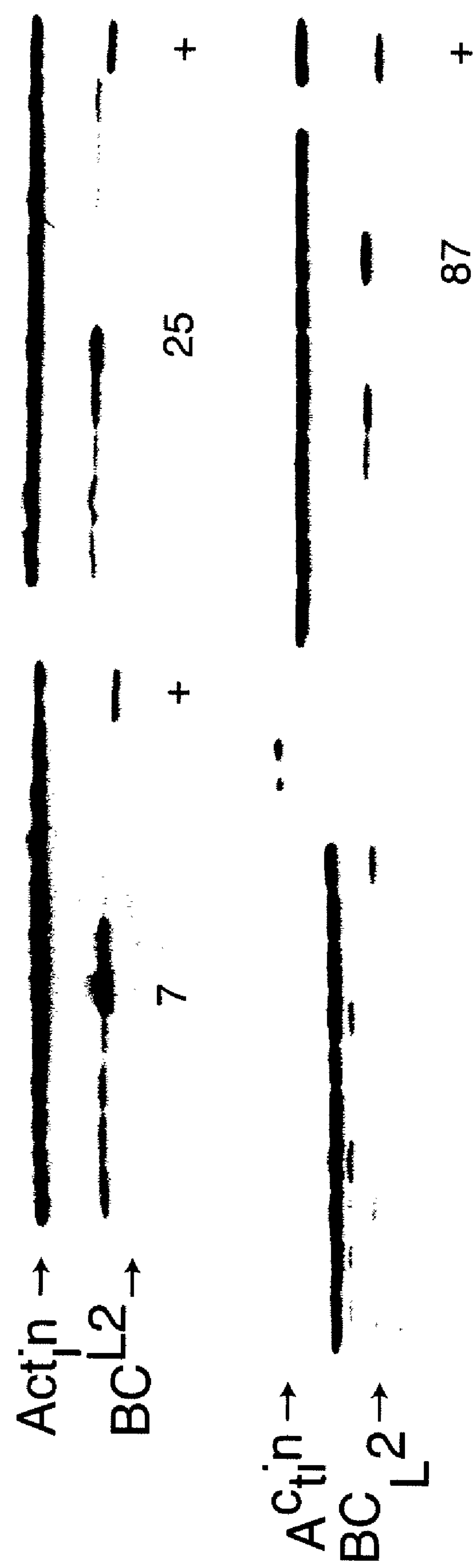

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, the term "about" means plus or minus ten percent. I.e., "about 100" means a number between 90 and 110.

An "antibody," as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

A "naked" antibody or fragment thereof refers to an antibody or fragment that is not conjugated to any therapeutic or diagnostic agent. A "conjugated" antibody or fragment thereof is used interchangeably with "immunoconjugate" to refer to an antibody or fragment thereof that is conjugated to at least one therapeutic or diagnostic agent.

An antibody fragment is a portion of an antibody such as $F(ab)_2$, $F(ab')_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

As used herein, the term antibody fusion protein refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

Optimizing Protein Production in Cell Culture

Various approaches have been employed to augment the maximal cell density and extend survival of mammalian cell cultures, which in turn results in increased protein yield. Most strategies include optimization of media formula and feeding routines to increase total cell number. One method to increase the lifespan of cells in culture is transfection of oncogenes, as exemplified by PER.C6, which is a human embryonic retinal cell line that has been immortalized with the adenovirus E1 gene (Jones, et al., 2003, Biotechnol Prog 19:163-168).

Optimizing media conditions and attempting to increase the culture lifespan may delay apoptosis. However, nutrient and oxygen depletion as well as metabolite accumulation are inevitable, and apoptosis will ultimately follow, which has been determined to be the primary mechanism of cell death in cell culture systems (Dickson, 1998, Trends Biotechnol 16:339-342; Fussenegger and Bailey, 1998, Biotechnol Prog 14:807-833; Singh and Al-Rubeai, 1998, Adv Biochem Eng Biotechnol 62:167-184).

Thus, eliminating premature death by averting or delaying apoptosis in cell culture systems is another promising approach, as exemplified by the introduction of anti-apoptotic genes, such as the Bcl-2 family members, including bcl-2 and bcl-$x_L$, into antibody-producing cell lines. Nevertheless, exogenous expression of wild-type bcl-2 and bcl-$x_L$ genes has resulted in limited protection from cell death and little or no improvement in antibody yields (Mastrangelo et al., 2000, Biotechnol Bioeng 67:555-564; Meents, et al., 1996, J Exp Med 183:2219-2226; Tey et al., 2000, Biotechnol Bioeng 68:31-43). More recent efforts have involved the use of mutant forms of these proteins. In one study, a Bcl-$x_L$ variant lacking most of the non-conserved unstructured loop domain was found to be effective in protecting CHO cells from apoptosis in response to serum deprivation than the wild-type Bcl-$x_L$ (Figueroa et al., 2003, Metab Eng 5:230-245). In another study, Deng et al. (2004, PNAS 101:153-158) demonstrated that over-expression of a mutant Bcl-2 possessing three point mutations (T69E, S70E and S87E), which mimics phosphorylation, exhibited significantly higher anti-apoptotic activity compared to wild-type Bcl-2.

In the present disclosure, described in the Examples below, we have stably transfected the murine myeloma cell line, Sp2/0-Ag14, with a similar Bcl-2 triple mutant to obtain a new host cell line (SpEEE) that exhibits enhanced survival and adaptability to growth in serum-free conditions. After one round of subcloning, a population of cells that exhibited robust growth was identified and named SpESF.

In a further attempt to improve the robustness of the cell line, SpESF cells were subject to iterative rounds of environmental insult by allowing the cells to overgrow until cell viability dropped to ~50-75%. The resulting subclones were designated SpESF-X (subclones #1-14). Each of the described cell lines has shown successful transfection and expression of appreciable levels of mAbs, making them suitable host cell lines for expression of mAbs and other recombinant proteins.

Cell Lines

Various embodiments of the present invention concern improved compositions, including host cell lines, and methods for enhanced production of recombinant proteins in such cell lines. Cell lines have been created that constitutively express one or more anti-apoptotic genes and that can be transfected with an expression construct encoding a protein or peptide of interest, where expression of the anti-apoptotic gene(s) prolongs survival of the transfected cell in culture and provides for enhanced yields of the protein or peptide of interest.

Specific embodiments concern derivatives of the Sp2/0 myeloma cell line that provide novel cell lines, referred to as Sp-E26, SpEEE, SpESF and SpESF-X, which show enhanced survival in batch culture. Sp-E26 constitutively expresses the E6 and E7 proteins of HPV-16. SpEEE, SpESF and SpESF-X constitutively express a Bcl-2 mutant, referred to as Bcl-2-EEE. In addition, recombinant protein production, and particularly production of recombinant antibodies and antibody fragments, can be improved upon transfecting Sp-E26, SpEEE, SpESF or SpESF-X with an expression vector for the recombinant protein of interest. The E6/E7 or Bcl-2-EEE proteins delay induction of apoptosis in the host cells and permit enhanced recombinant protein production in the host cells. Protein production can be boosted still further by addition of one or more caspase inhibitors (e.g., caspase 1 and/or 3 inhibitors) (Bin Yang et al. Nephron Experimental Nephrology 2004; 96:e39-e51), and/or by addition of one or more members of the cytokine type I superfamily, such as erythropoietin (EPO), into the growth medium of the cells. A pan-caspase inhibitor is particularly effective in this regard.

Further, the SpEEE cell line can be pre-adapted for growth and protein production in serum-free or low-serum conditions, resulting in serum-free pre-adapted cell lines such as SpESF or SpESF-X. The SpESF, SP-ESF-X and similar cell lines may be transfected with one or more expression vectors encoding a protein of interest, such as an antibody, antibody fragment, bispecific antibody, etc. The use of serum-free conditions for transfection, which is unique among mammalian cell lines available for transfection and protein production, saves a significant amount of time required for adaptation to serum-free growth.

In certain embodiments, such pre-adapted cell lines as SpESF or SpESF-X may be stored frozen and thawed prior to transfecting with one or more expression vectors encoding a protein of interest. This ability to "bank" frozen cell lines that are pre-adapted for growth, transfection and/or protein production in low serum or serum-free medium is unexpected and provides a substantial advantage over cell lines known in the prior art for cost, ease of use, rapidity of protein production and relative productivity of expressed proteins.

Production of recombinant proteins, such as antibodies or antibody fragments, can be significantly enhanced in the host cell by co-expression of an apoptosis inhibitor, such as Bcl-2. In particular, protein production is significantly enhanced in a myeloma cell line, such as Sp2/0, that is stably transfected with an expression vector encoding an antibody or antibody fragment and that is co-transfected with an expression vector encoding an apoptosis inhibitor, such as Bcl-2. Increased production of antibody can also be obtained from a host cell transfected with the E6/E7 gene. Recombinant protein production can be boosted still further by addition of one or more caspase inhibitors into the growth medium of the cells. A pan-caspase inhibitor is particularly effective in this regard. Also, recombinant protein production can be enhanced by feeding EPO, or another anti-apoptotic cytokine, into the medium of the cell culture.

Physiological, or programmed, cell death, referred to as apoptosis (Kerr et al., Br J. Cancer., 26:239-257, 1972), is essential for proper tissue development and maintenance and is controlled by an intrinsic genetic program that has been conserved in evolution (Ellis et al., Annu Rev Cell Biol, 7, 663-698, 1991). Hence, when cells grow in artificial environments, such as ex vivo cultures, this genetic endowment results in a finite lifespan. Therefore, the utility of such cell cultures for the production of proteins used in medicine and industry, as well as research, is dependent on maintaining such cultures for extended lifespan, or cycles, before they die according to apoptotic mechanisms.

Methods and agents have been discovered that act independently on cell proliferation and cell death events, by differentiating cell cycle from apoptotic effects. Bcl-2, a well-known intracellular regulator of apoptosis (Vaux et al., Nature 335, 440-2, 1988), is a proto-oncogene that has been found to have an anti-apototic effect that is genetically different from its inhibitory influence on cell cycle entry (Huang et al., EMBO J. 16, 4628-38, 1997). Two homologues of Bcl-2, Bcl-$x_L$ and Bcl-w, also extend cell survival, but other members of the Bcl-2 family, such as Bax and Bak, are pro-apoptotic (Oltvai et al., Cell 74, 609-19, 1993; Chittenden et al., Nature 374, 733-6, 1995; Farrow et al., Nature 374, 731-3, 1995; Kiefer et al., Nature 374, 736-9, 1995). Other anti-apoptotic genes include Bcl-6 and Mcl-1.

Thus, Bcl-2 and certain of its family members exert protection against apoptosis, and it may be used in a method to increase the lifespan of certain host cells in culture that are used for the production of proteins, thereby enhancing the amount of proteins produced and isolated. Over-expression of an anti-apoptotic Bcl-2 family member, such as Bcl-2, Bcl-$x_L$, Bcl-w or mutant varieties of these proteins, inhibits apoptosis, resulting in increased cell density and longer culture survival. Hence, transfection of anti-apoptotic Bcl-2 family genes avoids the necessity to prolong the cell culture by interfering with the cell cycle per se, as others have proposed (ibid.). Similarly, transfection of fibroblasts with genes for Bcl-2 results in over-expression of Bcl-2 in these cells, resulting in an antagonism of apoptosis and increasing the lifespan of these cells, with a concomitant increase in the production and isolation of recombinant proteins. It has also been observed that upon cytokine withdrawal, interleukin-6 (IL-6)-dependent murine myeloma cells expire as if they undergo apoptosis. It was also found that IL-6-receptors in such cells could be regulated by Bcl-2 or Bcl-$x_L$ in extending apoptosis (Schwarz et al., Cancer Res 55:2262-5, 1995).

It has been reported that a mutant Bcl-2 possessing three point mutations (T69E, S70E and S87E) exhibited significantly more anti-apoptotic activity compared to wild type or single point mutants (Deng et al., PNAS (101) 153-158, 2004). Thus, various embodiments concern the construction of an expression vector for a Bcl-2-EEE triple mutant, which was then used to transfect Sp2/0 cells to create SpEEE clones and subclones that show improved longevity and recombinant protein production.

Other agents, such as oncogenic viruses, can also oppose apoptosis as part of their eliciting cellular immortalization and ultimately complete malignant transformation, such as high-risk type HPV oncoproteins E6 and E7 (Finzer et al., Cancer Lett 188, 15-24, 2002). For example, the viral E6 protein effectively blocks the epidermal apoptotic response to ultraviolet light (Storey, Trends Mol Med 8, 417-21, 2002). It has also been suggested, from indirect evidence, that the human papillomavirus may cause reduced apoptosis in squamous (but not basal cell) carcinoma (Jackson et al., Br J Cancer 87, 319-23, 2002). However, not all papillomavirus oncoproteins have anti-apoptotic effects. For example, other studies have reported that the papillomavirus E6 protein of bovine species sensitizes cells to apoptosis (Liu et al., Virology 295, 230-7, 2002), which is in contrast to other studies showing that HPV-16 E7 gene protects astrocytes against apoptosis induced by certain stimuli (Lee et al., Yonsei Med J 42, 471-9, 2001). By use of E6-binding peptide aptamers, direct experimental evidence was obtained that HPV E6 oncoprotein has anti-apoptotic activity in HPV-positive tumor cells (Butz et al., Proc Natl Acad Sci USA 97, 6693-7, 2000). However, other HPV oncoproteins can have the opposite effect. The E2 protein induces apoptosis in the absence of other HPV proteins (Webster et al., J Biol Chem 275, 87-94, 2000).

Continuous expression of both the E6 and E7 proteins is known to be required for optimal proliferation of cervical cancer cells and the two viral proteins exert distinct effects on cell survival (DeFilippis et al., J Virol 77, 1551-63, 2003). The primary intracellular target attributed to HPV-16 E6 is p53. E6 forms a ternary complex with p53 and a cellular ubiquitin ligase, E6AP, resulting in the ubiquitination and degradation of p53 through the proteosome pathway and inactivation of p53. On the other hand, HPV-16 E7 protein interacts and destabilizes the tumor suppressor protein Rb. Moreover, levels of a variety of other intracellular proteins involved in apoptosis and cell cycle pathways were reported to be regulated by E6 and E7 transformation, such as Bcl-2, Bcl-$x_L$, p73, MDM2, p21, cyclins and cdc, cdk proteins, etc. Changes in the expression of these proteins will greatly influence the physiological properties of the cell. The present inventors therefore hypothesized that transfection of cells in culture by HPV-16E6 and E7 would be effective in generating genetically modified clones that are resistant to aging-culture-condition induced apoptosis and, therefore, prolong the lifespan of the cell culture. It was also postulated that introduction into a cell of either HPV-16 oncoprotein E7 or E6 alone might be sufficient to generate genetically modified clones with improved resistance to aging-culture-condition induced apoptosis. When the cell is a recombinant protein-producing clone, the improved physiological properties would in turn translate into enhanced overall protein productivity.

Generation of New Host Cells Expressing Viral Anti-Apoptotic Genes

Host cells, such as myeloma host cells, can be generated that constitutively express viral anti-apoptotic genes, such as HPV-16 E6 and E7 proteins. These host cells can be transfected with an expression vector that encodes a recombinant protein of interest and co-expression of the anti-apoptotic genes results in significantly increased production of the recombinant protein.

The host cell can be essentially any host cell suitable for recombinant protein production that can be stably transfected with the viral anti-apoptosis genes. For many recombinant proteins, host cells such as COS cells are advantageous, while for other proteins, such as antibodies, host cells such as myeloma cells are the common choices. Other examples of useful host cell lines are VERO and HeLa cells, W138, BHK, COS-7, 293, HepG2, 3T3, NSO, NS1, RIN and MDCK cell lines. Cell lines of use may be obtained from commercial sources, such as the COS-1 (e.g., ATCC CRL 1650), COS-7 (e.g., ATCC CRL-1651), HEK293, BHK21 (e.g., ATCC CRL-10), P3X3Ag8.653 (ATCC CRL-1580) and BSC-1 (e.g., ATCC CRL-26) cell lines. In preferred embodiments, the host cell is a mammalian cell line other than the CHO cell line. The viral (e.g., E6/E78) and/or eukaryotic genes can be introduced into the host cell by any suitable method that results in constitutive or inducible expression of the genes, i.e., any method that permits stable integration of the genes into the host cell chromosome while permitting expression of the genes. Methods for stable transfection of host cells with a gene of interest are well known in the art. A particularly advantageous method is to use a retroviral vector that encodes the viral anti-apoptosis genes. Suitable vectors include the LSXN vector (Miller et al. Biotechniques 7, 980-90, 1989). However, any alternative methods known in the art, such as electroporation or cell fusion, may be utilized.

In preferred embodiments, the Sp2/0 cell line is used as the host cell. More preferably, Sp2/0 is transfected with the triple mutant Bcl-2 gene to form the SpEEE host cell line. Even more preferably, the SpEEE cell line is pre-adapted to growth, transfection and protein production in serum-free medium to form a pre-adapted cell line such as SpESF. Most preferably, the SpESF cell line is grown under stressful growth conditions to form a highly robust, high productivity host cell line such as SpESF-X. SpESF-X may be grown, transfected with an expression vector and produce expressed proteins under serum-free conditions. Protein production from SpESF-X is surprisingly higher than known prior art cell lines, such as CHO cells.

Advantageously, the vector used to transfect the host cell contains a selectable marker that permits selection of cells containing the vector. Suitable selection markers, such as enzymes that confer antibiotic resistance on transfected cells, are well known in the art. After transfection, cells are maintained in a medium containing the selection agent, such as an antibiotic, and screened for resistance to the marker. Cells can be selected and cloned by limiting dilution using conventional methods.

The ability of the viral anti-apoptosis genes to increase cell viability can be tested by challenging the cells with an agent that induces apoptosis, such as cycloheximide (CHX). Cells that do not express the viral anti-apoptosis genes tend to demonstrate significant onset of apoptosis, whereas cells expressing the genes exhibit drastically reduced apoptotic activity. Methods of detecting apoptosis are well known in the art and include, for example, cell surface FITC-Annexin V binding assay, DNA laddering assay and TUNEL assay.

Upon selection of suitable cells expressing the viral anti-apoptosis genes, the cells can be transfected with an expression vector encoding the recombinant protein of choice. The expression vector can be a vector suitable for transient expression or, advantageously, can be an episomal vector containing a eukaryotic origin of replication, or an amplifiable vector that permits stable integration and subsequent gene amplification of the expression cassette. Suitable vectors are well known in the art and include, for example, the pdHL2 vector, which is particularly suited for production of antibodies and antibody fragments. When an amplifiable expression cassette is used, it advantageously contains a selectable marker that is different from the selectable marker used in the retroviral vector, to allow selection of transfected cells. Once again, suitably transfected cells can be selected and then cloned by limiting dilution.

Upon selection of suitable clones, the cells can be placed in a suitable medium and cultured to produce the desired protein of interest. The medium can contain serum or, preferably, be serum-free. In addition, cell longevity and protein production also can be increased by adding one or more caspase inhibitors (e.g., caspase 1 or 3) to the culture medium. Preferably the caspase inhibitor acts to inhibit one or more of caspase 3, caspase 9 and/or caspase 12. A cell-penetrating caspase inhibitor advantageously is used, and a pan-caspase inhibitor is particularly advantageous. Suitable inhibitors such as Z-VAD-fmk and Ac-DEVD-cho (SEQ ID NO: 7) are well known in the art. Alternatively, the cell line can be further transfected to express a caspase inhibitor, such as Aven or XIAP, to enhance its growth properties by affecting apoptosis. In this regard, certain members of the cytokine type I superfamily, such as EPO, can also increase cell survival by having anti-apoptotic and cytoprotective actions.

The methods described above generate a cell line that can be used for transfection with essentially any desired gene. However, the skilled artisan will recognize that established cell lines that constitutively express a desired protein, and particularly a recombinant protein, can be subsequently transfected with a suitable vector encoding the viral or Bcl-2 family anti-apoptosis genes. See Example 2 below.

Proteins and Peptides of Interest

The protein of interest can be essentially any protein that can be produced in detectable quantities in the host cell. Examples include traditional IgG type antibodies, Fab', Fab, $F(ab')_2$ or $F(ab)_2$ fragments, scFv, diabody, IgG-scFv or Fab-scFv fusion antibodies, IgG- or Fab-peptide toxin fusion proteins, or vaccines [e.g., including not limited to, Hepatitis A, B or C; HIV, influenza viruses, respiratory syncytial virus, papilloma viruses, Herpes viruses, Hantaan virus, Ebola viruses, Rota virus, Cytomegalovirus, *Leishmania* RNA viruses, SARS, malaria, tuberculosis (Mycobacteria), Anthrax, Smallpox, Tularemia, and others listed in the vaccines.org website, incorporated herein by reference in its entirety]. The host cells described herein are particularly suitable for highly efficient production of antibodies and antibody fragments in myeloma cell lines as described in Examples 1 and 2, as well as recombinant growth factors (e.g., EPO, G-CSF, GM-CSF, EGF, VEGF, thrombopoietin), hormones, interleukins (e.g., IL-1 through IL-31), interferons (e.g., alpha, beta, gamma, and consensus), and enzymes. These methods could be applied to any number of cell lines that are used for production of recombinant proteins, including other myeloma cell lines, such as murine NSO or rat YB2/0; epithelial lines, such as HEK 293; mesenchymal cell lines, such as fibroblast lines COS-1 or COS-7; and neuronal cells, such as retinal cells, as well as glial and glioma cells.

The skilled artisan will realize that a wide variety of nucleic acid sequences encoding potential proteins or peptides of interest are known in the art and any such known nucleic acid or known proteins or peptides may be utilized in or produced by the disclosed methods and compositions. In particular, the well-known GenBank database contains thousands of protein-encoding nucleic acid sequences, any one of which could potentially be used.

Exemplary proteins or peptides of interest that may be produced are discussed herein. The skilled artisan will realize that these are preferred embodiments only and do not limit the scope of the claimed subject matter. For example, MIF is a pivotal cytokine of the innate immune system and plays an important part in the control of inflammatory responses. Originally described as a T lymphocyte-derived factor that inhibited the random migration of macrophages, the protein known as macrophage migration inhibitory factor (MIF) was an enigmatic cytokine for almost 3 decades. In recent years, the discovery of MIF as a product of the anterior pituitary gland and the cloning and expression of bioactive, recombinant MIF protein have led to the definition of its critical biological role in vivo. MIF has the unique property of being released from macrophages and T lymphocytes that have been stimulated by glucocorticoids. Once released, MIF overcomes the inhibitory effects of glucocorticoids on TNF-α, IL-1 beta, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly useful in treating cancer, pathological angiogenesis, and sepsis or septic shock.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the proinflammatory cytokines IL-1 alpha, IL-6, IL-8, IL-12, TNF-α and RANTES. HMGB-1 released by necrotic cells may be a signal of tissue or cellular injury that, when sensed by DCs, induces and/or enhances an immune reaction. Palumbo et al. report that HMBG1 induces mesoangioblast migration and proliferation (*J Cell Biol,* 164:441-449 (2004)). HMBG-1 may be useful in treating sepsis and/or septic shock. Yang et al., *PNAS USA* 101:296-301 (2004); Kokkola et al., *Arthritis Rheum,* 48:2052-8 (2003); Czura et al., *J Infect Dis,* 187 Suppl 2:S391-6 (2003); Treutiger et al., *J Intern Med,* 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. One of the actions of TNF-α is appetite suppression.

Coagulation factors may also be of use, particularly tissue factor (TF) and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation. Genetic defects in production of one or more coagulation factors may result in hereditary anemia.

In rheumatoid arthritis, a recombinant interleukin-1 receptor antagonist, IL-1Ra or anakinra (Kineret®), has shown activity (Cohen et al., *Ann Rheum Dis* 2004; 63:1062-8; Cohen, *Rheum Dis Clin North Am* 2004; 30:365-80). An improvement in treatment of these patients, which hitherto required concomitant treatment with methotrexate, is to combine anakinra with one or more of the anti-proinflammatory effector cytokines or anti-proinflammatory effector chemokines. Indeed, in a review of antibody therapy for rheumatoid arthritis, Taylor (*Curr Opin Pharmacol* 2003; 3:323-328) suggests that in addition to TNF, other antibodies to such cytokines as IL-1, IL-6, IL-8, IL-15, IL-17 and IL-18, are useful. These and many other therapeutic proteins or peptides may be produced using the disclosed methods and compositions.

Recombinant Antibody Expression in Cells Expressing Apoptosis Inhibitors

Prior work has described the effects of co-expressing Bcl-2, a naturally occurring apoptosis inhibitor, in recombinant CHO cells producing a chimeric antibody. (See Tey et al., Biotechnol. Bioeng. 68:31-43 (2000).) Although increased cell culture life was observed, antibody production did not increase over equivalent cells that lacked Bcl-2 expression. Further, there was no evidence that the expression vector was stably transfected into the CHO cell line. However, the present inventors have found that production of recombinant antibody from myeloma cells is significantly increased when the cells also express Bcl-2. The Bcl-EEE transfected cell lines described below also evidence stable transfection of the expression vector(s), resulting in long-term protein production.

Advantageously, the myeloma cell line is stably transfected with an expression cassette encoding the antibody or antibody fragment. A suitable expression cassette contains one or more promoters that controls expression of the antibody heavy and light chains (or single chain in the case of an scFv) together with a selectable marker as described above. A particularly useful vector is pdHL2, which contains a selectable marker gene comprising a promoter operatively linked to a DNA sequence encoding a selectable marker enzyme; a transcription unit having a promoter operatively linked to a DNA sequence encoding the protein of interest; an enhancer element between the selectable marker gene and the transcription unit, which stimulates transcription of both the selectable marker gene and the first transcription unit compared to the transcription of both the selectable marker gene and the first transcription unit in the absence of the first enhancer.

The vector also contains a blocking element composed of a promoter placed between the first enhancer and the selectable marker gene, which is potentially useful for selectively attenuating the stimulation of transcription of the selectable marker gene. $V_H$ and $V_L$ sequences can be ligated into pdHL2, which is an amplifiable vector containing sequences for the human light chain constant region, the heavy chain constant region, and an amplifiable dhfr gene, each controlled by separate promoters. See Leung et al., Tumor Targeting 2:184 (1996) and Losman et al., Cancer 80:2660-2667 (1997). This vector can be transfected into cells by, for example, electroporation. Selection can be performed by the addition of 0.1 μM or a suitable concentration of methotrexate (MTX) into the culture media. Amplification can be carried out in a stepwise fashion with increasing concentration of MTX, up to 3 μM or higher. Cells stably transfected with the expression cassette and that constitutively express the antibody of interest can therefore be obtained and characterized using methods that are well known in the art. See also Example 4, below. After selection and cloning, the antibody-expressing cell line can then be transfected with an expression vector that encodes an anti-apoptosis gene, such as Bcl-2. For example, the vector pZeoSV (Invitrogen, Carlsbad, Calif.) containing the Bcl-2 gene fused to an SV40 promoter is transfected into the cell using a suitable method such as electroporation, and selection and gene amplification can be carried out if necessary.

Alternatively, a suitable host cell may be transfected with an apoptosis inhibitor, such as a mutant Bcl-2 gene, then adapted for growth in serum-free medium prior to further transfection, preferably in serum-free medium, with an expression vector encoding a desired protein of interest. Antibody production using the resulting cell line can be carried out as above and compared to production in cells that do not express an apoptosis inhibitor. Representative examples to illustrate the present invention are given below.

While preferred embodiments are illustrated herein by way of cell lines transfected with one or more genes encoding inhibitors of apoptosis known in the art, the skilled artisan will realize that in alternative embodiments, various substitutions, deletions or insertions may be made in the coding and/or non-coding sequence of such genes within the scope of the claimed methods and compositions, so long as the encoded protein exhibits the same physiological function (anti-apoptosis) as the native protein. In certain embodiments, the encoded protein(s) may exhibit 80% or greater sequence identity with the native (wild-type) protein, more preferably 85% or greater, more preferably 90% or greater, more preferably 95% or greater, more preferably 98% or greater, more preferably 99% or greater, most preferably 99.5% or greater sequence identity.

Antibodies

Various embodiments may concern antibodies and/or antibody fragments expressed from the transfected cell lines of interest. The term "antibody" is used herein to refer to any antibody-like molecule that has an antigen binding region, and includes antibody fragments such as Fab', Fab, $F(ab')_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies: A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and are available for use in the claimed methods and compositions. (See, for example, U.S. Pat. Nos. 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 8,783,758; 6,770,450; 6,767,711; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206' 6,441,143; 6,432,404; 6,432,402; 6,419,928; 6,413,726; 6,406,694; 6,403,770; 6,403,091; 6,395,274; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459 each incorporated herein by reference with respect to the ATCC deposit number for the antibody-secreting hybridoma cell lines and the associated target antigens for the antibodies or fragments thereof.) These are exemplary only and a wide variety of other antibody-secreting hybridomas are known in the art. The skilled artisan will realize that antibody-secreting hybridomas against almost any disease-associated antigen may be obtained by a simple search of the ATCC, PubMed and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Production of Antibody Fragments

Some embodiments of the claimed methods and/or compositions may concern antibody fragments. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY (John Wiley & Sons).

Other methods of forming antibody fragments, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.). Where an antibody-secreting hybridoma cell line is publicly available, the CDR sequences encoding antigen-binding specificity may be obtained, incorporated into chimeric or humanized antibodies, and used.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

EXAMPLES

Example 1

Generation of Apoptosis-Resistance Cell Clones by Stable Expression of HPV-16 E6 and E7 Genes Selection of Cell Clones Resistant to CHX Treatment Sp2/0 cells were transduced with an LXSN retroviral vector containing the expression cassette of HPV-16 E6 and E7 genes at an MOI (multiple of infection) of 10:1. After recovery for 24 h, the infected cells were selected in G418 (1000 μg/ml) for 10 days. G418-resistant cells were cloned in 96-well cell culture plates by limiting dilution (0.5 cells/well). Stable infectants were screened for resistance to treatment by cycloheximide (CHX), a potent apoptosis-inducing agent. Briefly, healthy cells (viability>95%) were incubated in medium containing 25 μg/ml of CHX and cell morphology was examined under a microscope. While more than 50% of parent Sp2/0 cells underwent morphology change after two to three hours of incubation and became fragmented (not shown), several E6/E7 transfected clones showed less extent of morphology change, indicating resistance to apoptosis. The best clone, designated as Sp-E26, showed no apparent morphology change upon four hours of treatment (not shown).

The MTT assay was used to access the changes in viable cell population. After the healthy cells were incubated with or without CHX under normal culture condition for 2-3 h, MTT dye was added to the wells. After further incubation for two hours, the cells were solubilized by adding a lysis buffer contain SDS and HCl. The plates were incubated overnight at 37° C. and OD reading was performed at 590 nm using an ELISA plate reader. The viable cell population was significantly reduced when Sp2/0 cells were treated with CHX. By comparison, under the same treatment conditions (concentration of CHX and length of time), Sp-E26 cells tolerated better against CHX treatment (not shown). With this method, a large number of clones can be screened and selected for further analyses.

Anti-Apoptosis Property of Sp-E26

CHX-induced apoptosis in Sp-E26 and the parent Sp2/0 cells was evaluated by Annexin V staining and DNA fragmentation assay. After being incubated in the medium containing 25 μg/ml of CHX, the cells were harvested and stained with Guava Nexin reagent (equivalent of Annexin V staining) and analyzed in a Guava Personal Cell Analysis system (Guava Technologies, Inc.). More than 30% of Sp2/0 cells became Annexin V positive when exposed to CHX treatment for about 1.5 h, indicating apoptosis, while Sp-E26 remained healthy, showing no increase in early apoptotic cells (not shown).

The induction of apoptosis by CHX can be revealed by analysis of the formation of intracellular oligonucleosomal DNA fragments, a hallmark of apoptosis. The cellular DNA was extracted from CHX-treated and untreated Sp-E26 and Sp2/0 cells and DNA laddering assay was performed. In Sp2/0 cells treated with CHX, extensive DNA fragmentation was detected (not shown). In contrast, under identical treatment conditions, the genomic DNA of Sp-E26 was still intact, showing no appearance of DNA fragmentation (not shown).

Presence of HPV E6 and E7 Genes in Sp-E26 Cells

To confirm that E6 and E7 genes are stably present in the genome of Sp-E26 cells, oligonucleotide primers specific for E6 and E7 genes were designed and used in a PCR reaction with the genomic DNA extracted from Sp-E26 as the template, resulting in an about 700 bp DNA fragment. The PCR product was cloned and confirmed to be E6 and E7 genes by DNA sequencing (not shown). No E6 and E7 genes were detected in the parent Sp2/0 cells.

Improved Growth Properties of Sp-E26

The growth properties of Sp-E26 were evaluated in T-flask and 3 L-batch bioreactor. Sp-E26 showed improved growth properties over the parent Sp2/0 cell in batch cultures, achieving higher maximum cell density and longer survival time (not shown).

Example 2

Generation of Apoptosis-Resistance Cell Clones by Stable Over-Expression of HPV16 E7 Gene The structure of the poly-cistronic HPV 16 E6 and E7 genes integrated into the genome of clone Sp-E26 was analyzed by PCR using the primer pair E6-N8$^+$ (ATGTTTCAGGACCCACAGGAGCGA; SEQ ID NO: 8) and E7-C8- (TTATGGTTTCTGAGA ACAGATGGG; SEQ ID NO: 9) and DNA sequencing. Since the sequences of primer E6-N8$^+$ and E7-C8$^-$ match with the coding sequence for the N-terminal 8 amino acid residues of E6 and the complementary sequence for the C-terminal 8 codons of E7, respectively, the amplicon of full-length E6 and E7 is expected to be about 850 bp. However, amplification of the genomic DNA prepared from Sp-E26 cell with E6-N8$^+$ and E7-C8$^-$ resulted a PCR fragment of only about 700 bp. DNA sequencing of the 700 bp PCR product revealed a deletion of a 182 poly-nucleotide fragment from the E6 gene. The defective E6 gene likely resulted from splicing and encodes a truncated E6 peptide with N-terminal 43 amino acid residues. Considering the major physiological activity attributed to E6 is its ability to down-regulate p53 expression, the truncated E6 protein is probably not fully functional because the level of p53 expression in Sp-E26 was found to be more stable than that in Sp2/0.

Thus, to evaluate whether HPV-16 E7 gene alone is sufficient to have anti-apoptotic effect and to improve the growth properties of Sp2/0 cells, transfection of Sp2/0 cell with HPV-16 E7 is performed as follows:

(i) The DNA sequence encoding E7 is cloned from Sp-E26 cell by RT-PCR. Proper restriction sites are introduced to facilitate the ligation of the gene into a mammalian expression vector, pRc/CMV (Invitrogen). Transcription of the viral gene within the vector, designated as E7pRc, is directed from CMV promoter-enhancer sequences. The vector also contains a gene conferring neomycin resistance, which is transcribed from the SV40 promoter.

(ii) Sp2/0 cells are transfected with the expression vector containing the expression cassette of HPV-16 E7 gene. Briefly, 5 μg of E7pRc is linearized by ScaI and transfected into the cell by electroporation.

(iii) After recovery for 24 hours, the transfected cells are selected in G418 (1000 μg/ml) for 10 days.

(iv) G418-resistant cells are then cloned in 96-well cell culture plates by limiting dilution (0.5 cells/well). Stable transfectants are selected and screened for resistance to treatment by cycloheximide (CHX), a potent apoptosis-inducing agent.

(v) Healthy cells (viability >95%) are incubated in medium containing 25 μg/ml of CHX or in the absence of CHX for 3-4 hours under normal culture conditions, followed by the addition of MTT dye into the wells. After further incubation for two hours, the cells are solubilized by adding a lysis buffer contain SDS and HCl. The plates are incubated overnight at 37° C. and an OD reading is performed at 590 nm using an ELISA plate reader. Cell clones showing resistance to CHX treatment are selected and expanded for further analyses.

(vi) The anti-apoptosis property of E7-transfected cells is evaluated by Annexin V staining and DNA fragmentation assays. In the Annexin V assay, after being incubated in the medium containing 25 μg/ml of CHX, the cells are harvested and stained with Guava Nexin reagent (equivalent of Annexin V staining) and analyzed in a Guava Personal Cell Analysis system (Guava Technologies, Inc.). In the DNA fragmentation assay, the cellular DNA is extracted from CHX-treated and untreated E7-transfectants and Sp2/0 cells and analyzed with agarose gel electrophoresis.

(vii) Expression of the viral oncogene in E7-transfectants is evaluated by Southern blot (genomic level), Northern blot (mRNA level), and immunoblot (protein level) analysis. Expression of intracellular proteins that are involved in apoptosis processes and affected by E7 protein are examined by immunoblotting analyses.

(viii) The growth properties of selected E7-transfectants are evaluated in T-flask and in a 3 L-batch bioreactor. The transfectants showing improved growth properties, i.e. achieving higher maximum cell density and longer survival time, over the parent Sp2/0 cell in batch cultures are considered to be better host cells.

Example 3

High-Level Expression of hLL2 IgG in Sp-E26

In this example, Sp-E26 is used as a host to generate cell clones producing hLL2 (epratuzumab), a humanized anti-CD22 Ab developed for treating patients with NHL and autoimmune diseases. An hLL2-producing clone, 87-2-C9, was previously generated by using Sp2/0 cell as a host (Losman et al., Cancer 80, 2660-2666, 1997), in which case, only one positive clone (a frequency of about $2.5\times10^{-7}$) was identified after transfection, and the maximum productivity ($P_{max}$), defined as the concentration of the antibody in conditioned terminal culture medium in T-flask, of the only hLL2-producing clone, before amplification, was 1.4 mg/L. Transfection of Sp-E26 cell with the same hLL2pdHL2 vector and by using similar procedures as described by Losman et al. (Cancer 80, 2660-2666, 1997) resulted in more than 200 stable hLL2-producing clones, a frequency of $>10^{-4}$). The $P_{max}$ of 12 randomly selected clones was evaluated and found to be between 13 and 170 mg/L, with a mean of 50 mg/L. The productivities of these clones can be further enhanced by gene amplification with MTX. This example demonstrated the advantage of using Sp-E26 over its parent Sp2/0 cell as a host for the development of cell clones producing recombinant proteins.

Example 4

Improvement of Ab-Producing Cell Lines by Stable Expression of HPV16 E6 and E7 Genes 607-3u-8 cells were originally generated from Sp2/0 by transfection to produce a humanized monoclonal Ab. The clone was developed by gene amplification (with MTX) and subcloning to enhance the maximum (Ab) productivity up to 150 mg/L, which decreased to about 100 mg/L following weaning off serum supplement in the culture medium. To obtain higher antibody productivity under serum-free conditions, E6/E7 genes of HPV-16 were introduced into 607-3u-8 and the effect of E6/E7 on Ab-productivity was evaluated as follows.

607-3u-8 cells maintained in HSFM supplemented with 10% FBS and 3 μM MTX were transduced with an LXSN retroviral vector containing the expression cassette of HPV-16 E6 and E7 genes at an MOI of 10:1. After recovery for 24 h, stably transfected cells were selected in G418 (400 μg/ml) for 10 days. G418-resistant cells were subcloned in 96-well cell culture plates by limiting dilution (0.5 cells/well). A surviving clone, designated as 607E1C12, was obtained for evaluation. Two subclones, designated as 607-3u-8-7G7 and 607-3u-8-2D10, of 607-3u-8 without E6/E7 transfection were also selected. The $P_{max}$ of these three clones were determined and there were no significant difference (Table 1).

These results suggest that introducing E6/E7 genes into the cell does not alter the ability of cells producing Ab. Next, 607E1C12, 607-3u-8-7G7 and 607-3u-8-2D10 were adapted to grow in serum-free medium and the productivities of these clones were determined. All cells were growing well in serum-free medium. The final antibody productivity of clone 607E1C12 was maintained at 150 mg/L, while the two clones without E6/E7 were substantially reduced. In addition, the productivity of 607E1C12 was stable after a freeze (for cryopreservation) and thaw cycle (Table 1).

TABLE 1

The productivities of Ab-producing clones

| Clone | $P_{max}$ (mg/L)[a] | |
|---|---|---|
| | With serum | Serum-free |
| 607-3u-8-7G7 | 127 ± 16 (3)[b] | 74 ± 10 (4) |
| 607-3u-8-2D10 | 140 ± 4 (3) | 35 ± 2 (2) |
| 607E1C12 | 154 (1) | 142 ± 13 (6) |
| 607E1C12 (Cryo)[c] | | 145 ± 17 (5) |

[a]Determined by protein purification of IgG from terminal culture supernatants.
[b]The number in parenthesis indicates the sample size.
[c]Cells had been frozen for cryopreservation.

Example 5

Figure 11:
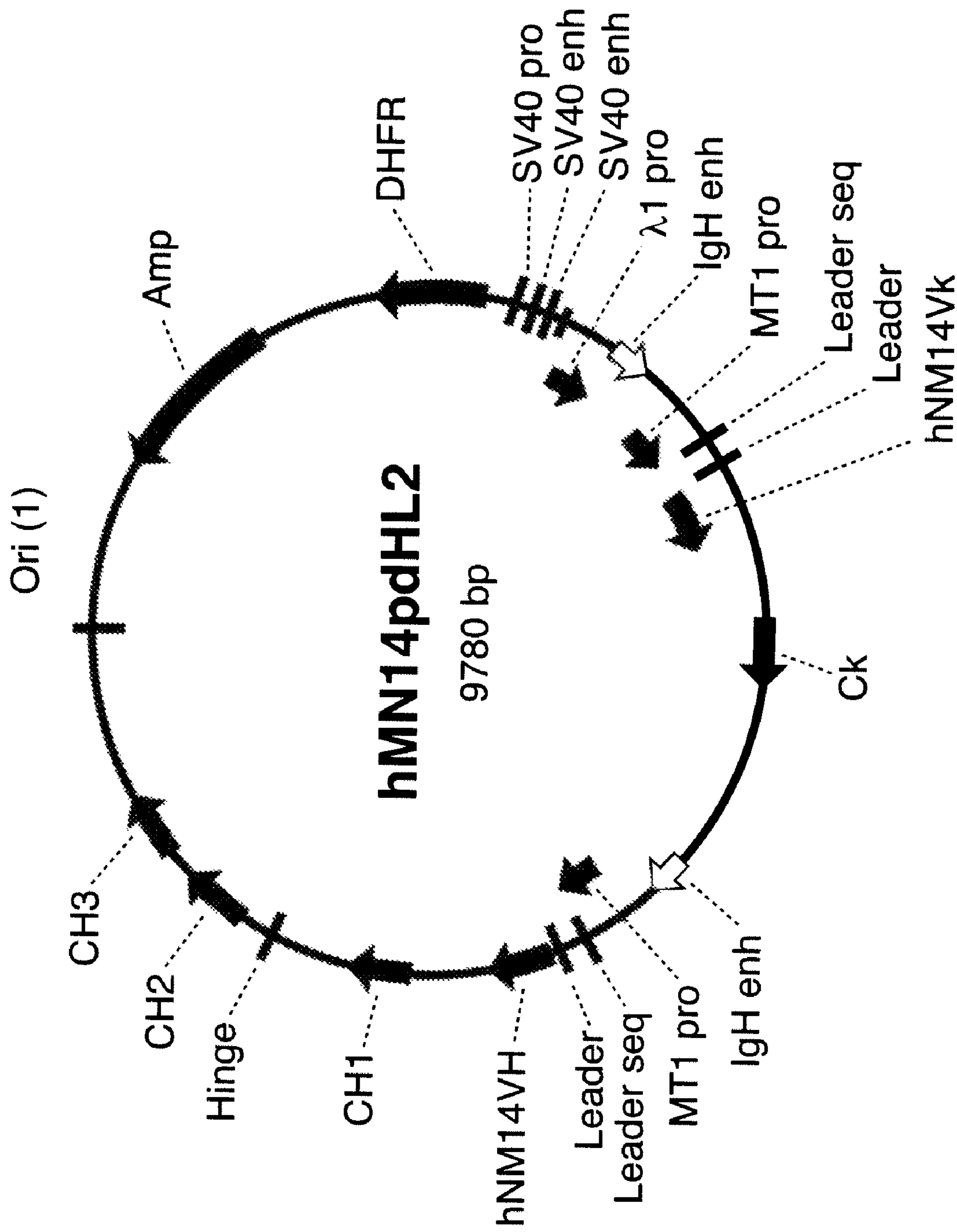
FIG. 11 shows the map of the pdHL2 vector used to transfect Sp2/0 cells to obtain the 665.2B9 clone with humanized antibody sequences and the SV40 promoter and enhancer sequences.

Improvement of Ab-Producing Cell Survival in Stationary Batch Culture by Stable Expression of a Human Bcl-2 Gene Generation of a Bcl-2-Transfected Cell Clone A cell clone 665.2B9 was originally generated from Sp2/0 by transfection to produce a humanized monoclonal anti-CEA Ab, or hMN-14 [labetuzumab] (Qu et al., unpublished results). A vector, designated hMN14pdHL2, was used to transfect Sp2/0 cells to obtain the cell clone 665.2B9. The pdHL2 vector was first described by Gillies et al., and had an amplifiable murine dhfr gene that allows subsequent selection and amplification by methotrexate treatment (Gillies et al., J. Immunol. Methods 125:191 (1989)). Generally, the pdHL2 vector provides expression of both IgG heavy and light chain genes that are independently controlled by two metallothionine promoters and IgH enhancers. A diagram of the hMN14pdHL2 vector is shown in FIG. 11. SEQ ID NO. 1 shows the sequence of the vector. SEQ ID NO. 2 shows the 72 bp sequence defined as the enhancer sequence; the promoter sequence corresponds to nt2908-2979 of hMN14pdHL2.

Sp2/0 cells can be generally transfected by electroporation with linearized pdHL2 vectors such as the hMN14pdHL2 vector used in this instance. Selection can be initiated 48 hours after transfection by incubating cells with medium containing 0.05 to 0.1 μM MTX. Amplification of inserted antibody sequences is achieved by a stepwise increase in MTX concentration up to 5 μM.

Figure 12:
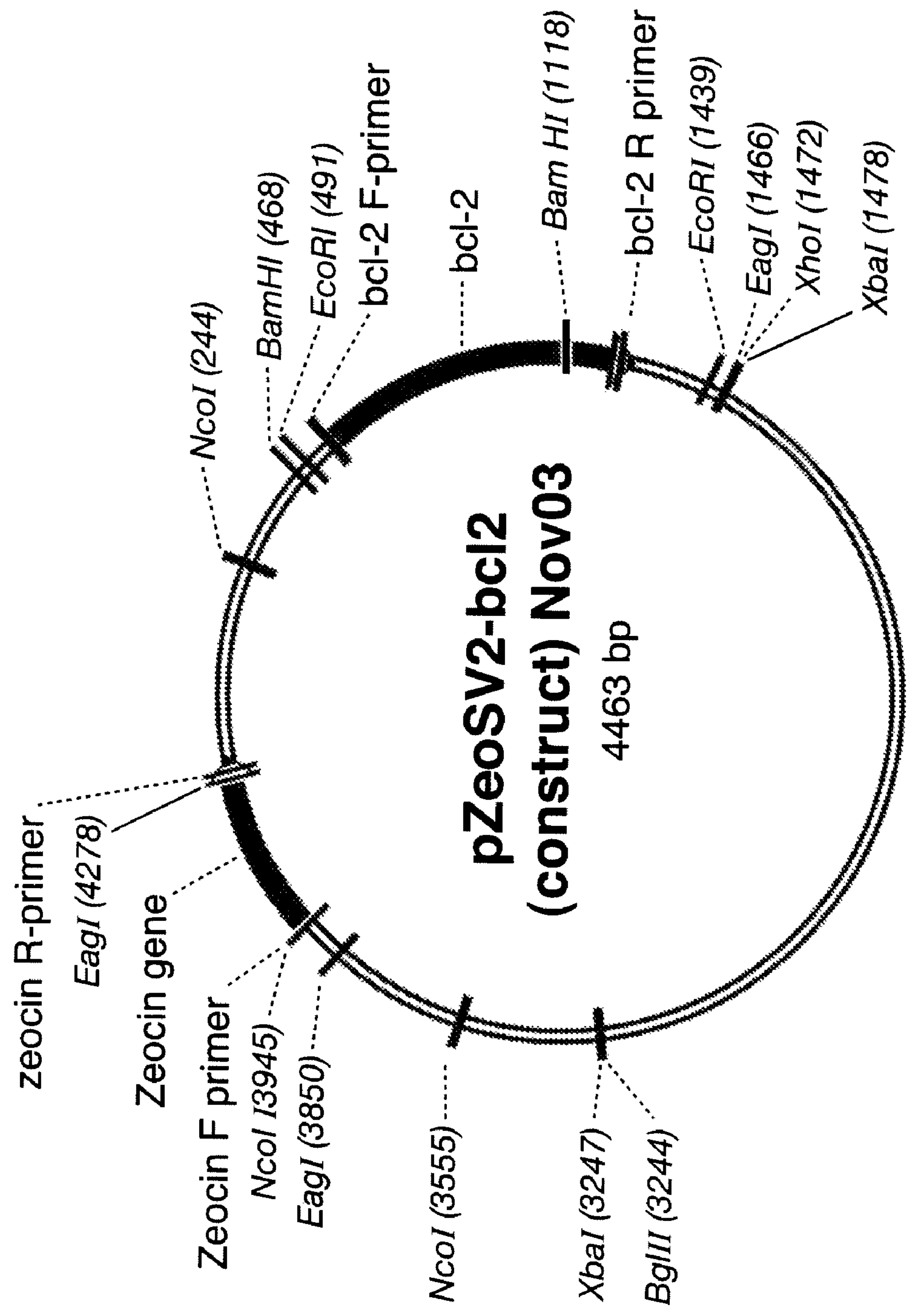
FIG. 12 shows the map of DNA plasmid with incorporated Bcl-2 gene, used for transfection of clone 665.2B9

The clone was subjected to gene amplification with MTX increased stepwise to 0.3 μM, at which point the maximum productivity (Pmax) of the antibody was increased to about 100 mg/L. To improve cell growth properties, 665.2B9 cells were transfected with a plasmid expression vector (FIG. 12) containing the human Bcl-2 gene by electroporation. Bcl-2 gene was excised from pB4 plasmid purchased from ATCC (pB4, catalog #79804) using EcoRI sites and inserted into MCS of mammalian expression vector pZeoSV(+) using the same restriction enzyme. Since zeocin resistance gene is part of the vector, transfected cells were placed into medium containing zeocin ranging from 50-300 μg/mL. Stable clones were selected from media containing 300 mg/ml zeocin and subcloned in media without zeocin by plating into 96-well plates at a density of 0.5 cell/100 uL/well. The media without zeocin was used thereafter.

Formation of clones in wells was confirmed by visual observation under a microscope. Cells from the wells with only 1 cluster of cells were expanded. Each 96-well plate produced around 30 clones, from which 14 clones were randomly selected for further studies. The growth characteristics of these clones were evaluated by daily cell counting and viability measurements with ViaCount reagent and Guava PCA. From the 14 clones evaluated in 24-well plates, one Bcl-2-transfected clone showing improved growth characteristics (higher cell densities and prolonged cell survival) was identified and designated as 665.2B9#4 (or clone #4). Comparing to the parent 665.2B9 clone, clone #4 grew to a higher cell density (about 1.7-fold) and survived 4 to 6 days longer in T-flasks (not shown), and as a consequence of better growth, the $P_{max}$ of clone #4 was increased to about 170 mg/L as determined by ELISA titration and Protein A column purification.

Bcl-2 Expression in 665.2B9#4

To confirm that the improved growth properties of 665.2B9#4 resulted from transfection of Bcl-2, intracellular level of human Bcl-2 protein was measured by using Guava Express reagent and Guava PCA instrument. Briefly, $4\times10^5$ cells placed in 1.5 ml spin-tubes were centrifuged for 5 minutes at 1500 rpm, washed three times with 1×PBS. Supernatants were carefully aspirated. Fixation solution (10×, 60 μL) from Santa Cruz Biotechnology (SCB), Inc. (cat. # sc-3622) was added to cell pellets for 15 min and incubated on ice. Fixation solution was removed with 4×1 mL PBS at 4° C., each time spinning as described.

Permeabilization buffer (0.5 mL) at −20° C. (SCB cat. # sc-3623) was added dropwise while vortexing, followed by 15 min incubation on ice. Cells were then spun and washed two times with 0.5 mL FCM wash buffer (SCB cat. # sc-3624). Final cell pellet was resuspended in 100 μL of FCM wash buffer and stained for Bcl-2 intracellular protein with 10 μL of anti-Bcl-2 mouse monoclonal antibody conjugated to PE (obtained from SCB). Incubation was performed at room temperature in dark for one hour. Two washes with 0.5 mL of FCM wash buffer followed. The final cell pellet was resuspended with 0.4 mL FCM wash buffer and the cells analyzed on Guava PC. Mean values of the fluorescence intensity (MFI) for each clone were compared to control staining with non-specific, isotype mouse IgGI conjugated with PE. The results summarized in Table 2 confirm that clone 665.2B9#4 expresses a higher level of Bcl-2 protein compared to the parental cell line. A zeocin-resistant clone (#13) that showed a similar growth profile as the parent 665.2B9 was negative for Bcl-2 staining, confirming that Bcl-2 expression is necessary for the improvement of growth.

TABLE 2

Intracellular level of Bcl-2 determined by Guava Express.

| Cell | Viability[a] (%) | Mean FI (AU) |
| --- | --- | --- |
| 665.2B9 | 84 | 42 |
| 665.2B9#4 | 97 | 110 |
| Clone#13 | 92 | 14 |
| Non-specific antibody staining | | 12 |

[a]Determined before the assay to ensure healthy cells were used.
[b]665.2B9 cells stained with an isotype-matched mouse IgG1 antibody, PE-conjugated.

With Guava Express analysis it was found that the intensities of fluorescent staining corresponding to Bcl-2 levels are rising with MTX amplification of clone 665.2B9#4, suggesting co-amplification of Bcl-2 with the dhfr gene. To compare intracellular Bcl-2 levels of amplified cells, Western blotting analysis was performed on cell lysates of clone 665.2B9#4 (Bcl-2 positive) and clone #13 (Bcl-2 negative) using an anti-human Bcl-2 antibody. Densitometric evaluation showed that Bcl-2 signal of clone 665.2B9#4 growing in 1.0 μM MTX is 2× stronger than the cells in 0.6 μM MTX. A lysate of Clone #13 did not reveal the presence of Bcl-2 protein (not shown).

Example 6

Generation and Characterization of the SpEEE Cell Line that Constitutively Expresses a Mutant Bcl-2

Evidence suggests that a mutant Bcl-2 possessing three point mutations (T69E, S70E and S87E) exhibits significantly more anti-apoptotic activity compared to wild type or single point mutants (Deng et al., PNAS 101: 153-158, 2004). Thus, an expression vector for this triple mutant (designated as Bcl-2-EEE) was constructed and used to transfect Sp2/0 cells for increased survival and productivity, particularly in bioreactors. Clones were isolated and evaluated for Bcl-2-EEE expression level, growth and apoptotic properties. The nucleic acid sequence for the Bcl-2-EEE is depicted as SEQ ID NO. 3; the corresponding amino acid sequence for the Bcl-2-EEE protein is depicted as SEQ ID NO. 4.

Molecular Cloning

A 116 bp synthetic DNA duplex was designed based on the coding sequence for amino acid residues 64-101 of human Bcl-2. The codons for residues 69, 70 and 87 were all changed to those for glutamic acid (E). The entire sequence was extraordinarily GC rich and had numerous poly G and poly C runs. Conservative changes were made to several codons to break up the G and C runs and decrease the overall GC content.

Two 80-mer oligonucleotides, BCL2-EEE Top and BCL2-EEE Bottom, were synthesized that, combined, span the 116 bp sequence and overlap on their 3' ends with 22 bp. The oligonucleotides were annealed and duplex DNA was generated by primer extension with Taq DNA polymerase. The duplex was amplified using the PCR primers BCL2-EEE PCR Left and BCL2-EEE PCR Right. The DNA sequences of these four oligonucleotides are provided below.

```
BCL2-EEE Top
                                              (SEQ ID NO:5)
5'GGACCCGGTCGCCAGAGAAGAACCGCTGCAGACTCCGGCTGCTCCTGG
AGCAGCTGCAGGACCTGCGCTCGAACCGGTGC-3'

BCL2-EEE Bottom
                                              (SEQ ID NO:6)
5'CGCCGGCCTGGCGGAGGGTCAGGTGGACCACAGGTGGCACCGGTTCGA
GCGCAGGTCCTGCAGCTGCTCCAGGAGCAGCC-3'

BCL2-EEE PCR Left
                                             (SEQ ID NO:10)
5'-TATATGGACCCGGTCGCCAGAGAAG-3'

BCL2-EEE PCR Right
                                             (SEQ ID NO:11)
5'-TTAATCGCCGGCCTGGCGGAGGGTC-3'
```

The 126-bp amplimer was cloned into the pGemT PCR cloning vector (Promega, Madison, Wis.) and the resulting vector (BCL2-EEE-pGemT) was digested with TthI and NgoMI restriction endonucleases to obtain the 105-bp fragment, which was ligated with hBCL2-puc19 vector (ATCC 79804) that had been digested with TthI and NgoMI to generate hBCL2(EEE)-puc19. The sequence of this construct was confirmed.

A 948-bp insert fragment was excised from hBCL2(EEE)-puc19 with EcoRI and ligated with pZeoSV2+ vector (Invitrogen, Carlsbad, Calif.) that was digested with EcoRI and treated with alkaline phosphatase. Insertion in the proper orientation was confirmed by digestion with BamHI with a correct clone having 650 bp and 3812 bp fragments (reverse orientation has 344 bp and 4118 bp). The resulting construct was designated hBCL2(EEE)-pZeoSV2+.

Cell Culture

Sp2/0-Ag14 cells (ATCC CRL# 1581), and SpEEE cells were maintained as suspension cultures in Hybridoma Serum-Free Media (H-SFM) supplemented with 10% fetal bovine serum (FBS), 4 mM L-glutamine and 100 units/ml penicillin-streptomycin (10% H-SFM; Invitrogen Life Technologies, Carlsbad, Calif.). Cell culture flasks, plates, vials and tubes were purchased from Corning (Lowell, Mass.). All cells were passaged in T-25 flasks at 37° C. and 5% $C0_2$. Viable cell concentration and percent viability were determined at each passage using Guava ViaCount and Guava PCA instrumentation (Guava Technologies, Inc., Hayward, Ca.)

Transfection of Sp2/0 Cells with hBCL2(EEE)-pZeoSV2+

Sp2/0 cells ($5.6\times10^6$) were then transfected by electroporation with 60 μg of hBcl-2 (EEE)-pZeoSV2+ via electroporation (450 volts, 25 μF) using a Gene Pulser electroporation apparatus (BioRad, Hercules, Calif.). Cells were resuspended in 60 ml of 10% H-SFM and plated onto six 96-well tissue culture plates. After 48 hours, 10% H-SFM containing zeocin, at a final concentration of 1.6 mg/ml, was added to each well. Zeocin-resistant clones were expanded for evaluation of Bcl-2-EEE expression.

Cells from 40 wells were expanded to 24-well plates and analyzed by Western blot with anti-hBcl-2 and anti-beta actin. All but 5 of the 40 showed medium to high levels of Bcl-2-EEE expression (not shown) An Sp2/0 derived hMN 14 cell line (Clone 664.B4) that was previously transfected with wild type Bcl-2 was used as a positive control. As was demonstrated by Deng et al., the Bcl-2-EEE migrates slightly slower than wild type Bcl-2 in SDS-PAGE.

Figure 2:
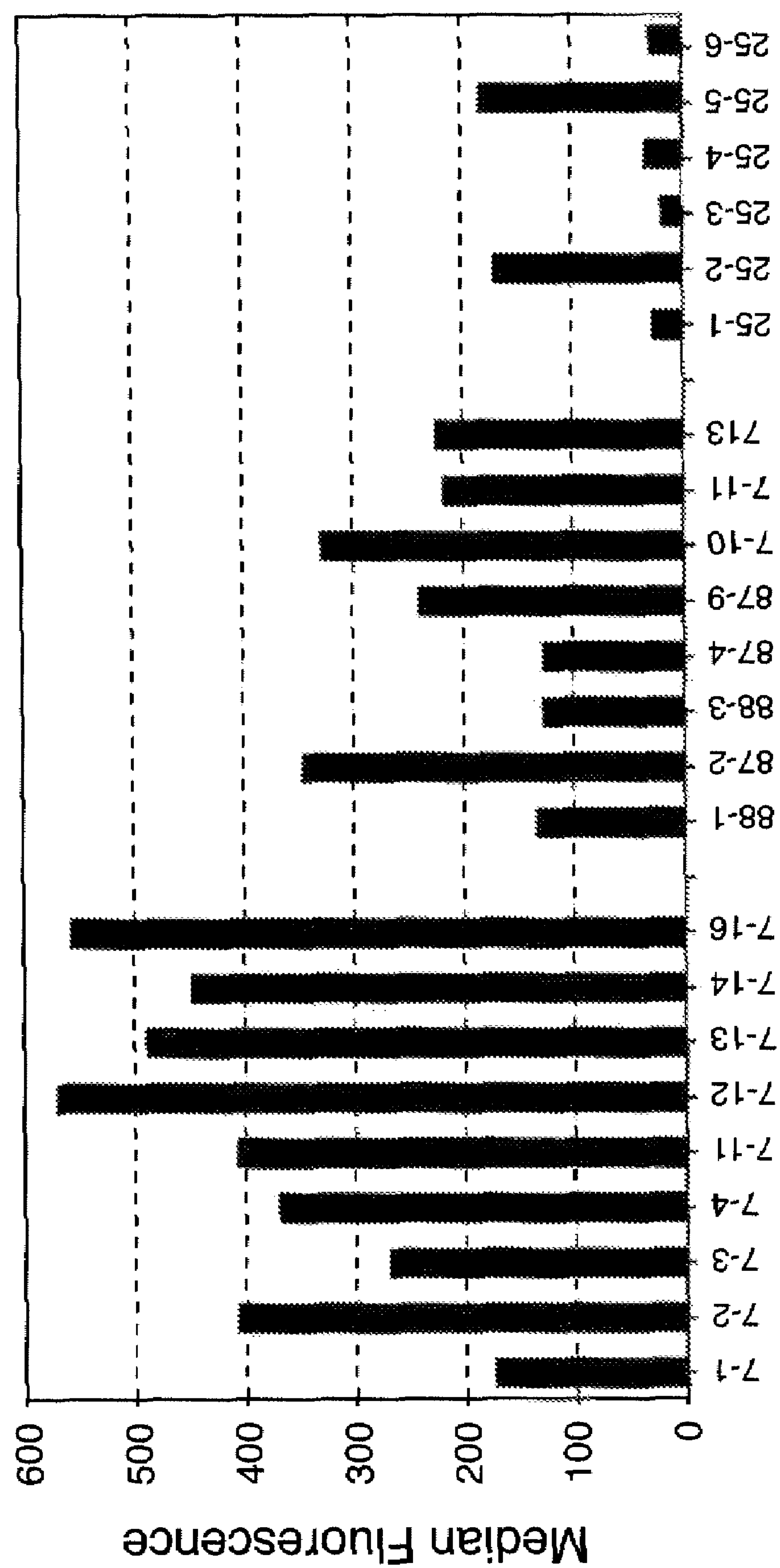

A transgene encoding a constitutively active Bcl-2 mutant was stably transfected into Sp2/0-Ag14 myeloma cells. Previously, the triple-mutant Bcl-2 (T69E, S70E and S87E) was shown to potently enhance survival of multiple cell lines in response to stress (Deng et al., 2004). Over-expression of the anti-apoptotic protein may lead to improved growth characteristics and enhance performance of a host cell line used for the production of antibodies and other proteins. Forty random transgenic clones were evaluated for Bcl-2 expression by anti-Bcl-2 immunoblotting (FIG. 1). Three of the strongest positive clones (#7, 25, and 87) were subcloned by limiting dilution and further analyzed for Bcl-2 expression using Guava Express (FIG. 2). Clones #7-12, 7-16, 87-2 and 87-10 were expanded for further analysis. Subsequently, some initially slower growing subclones were similarly analyzed and one clone, 87-29, gave a signal that was 20% higher than any other clone and was expanded for further analysis.

Figure 3A:
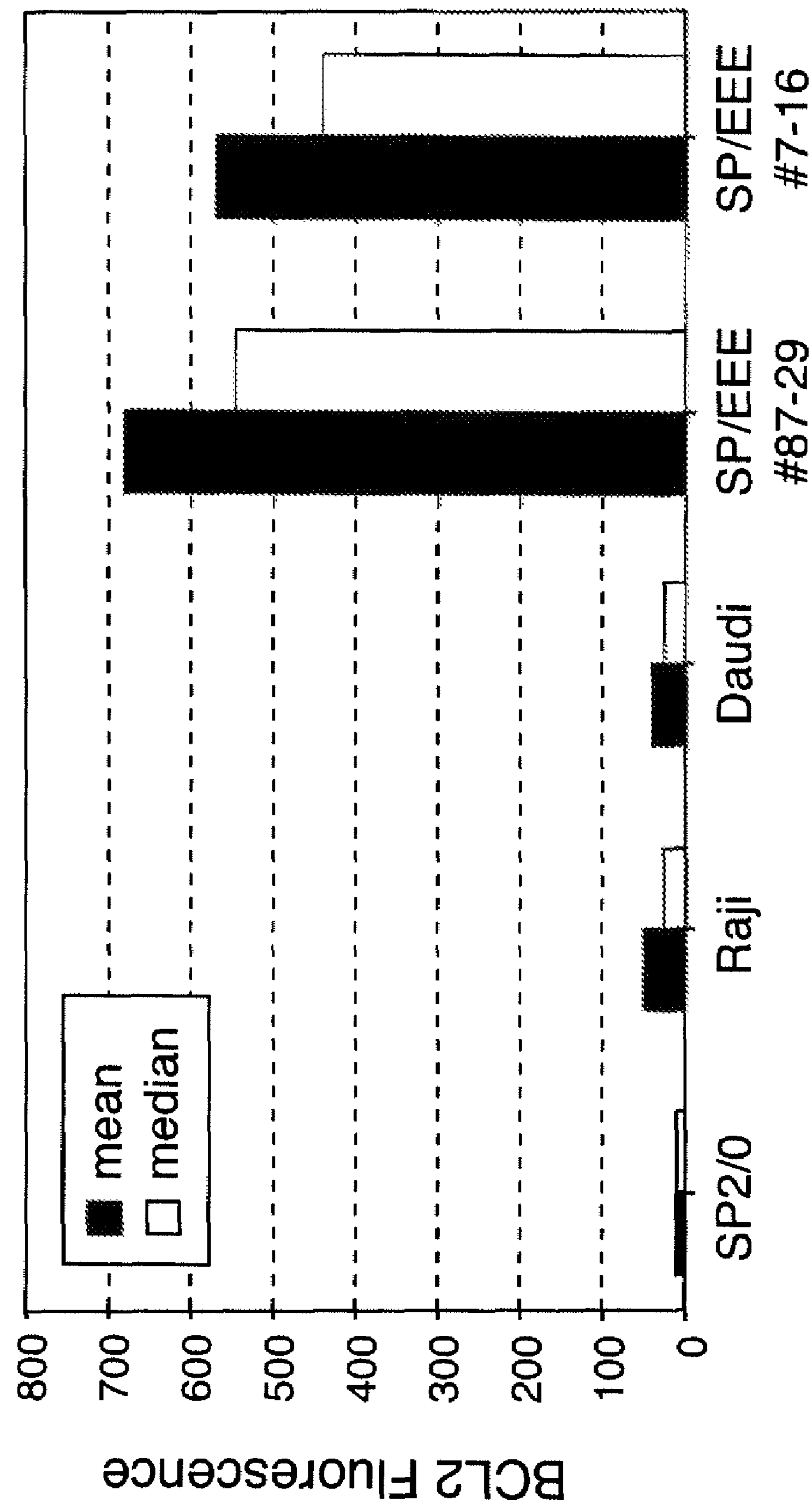
Figure 3B:
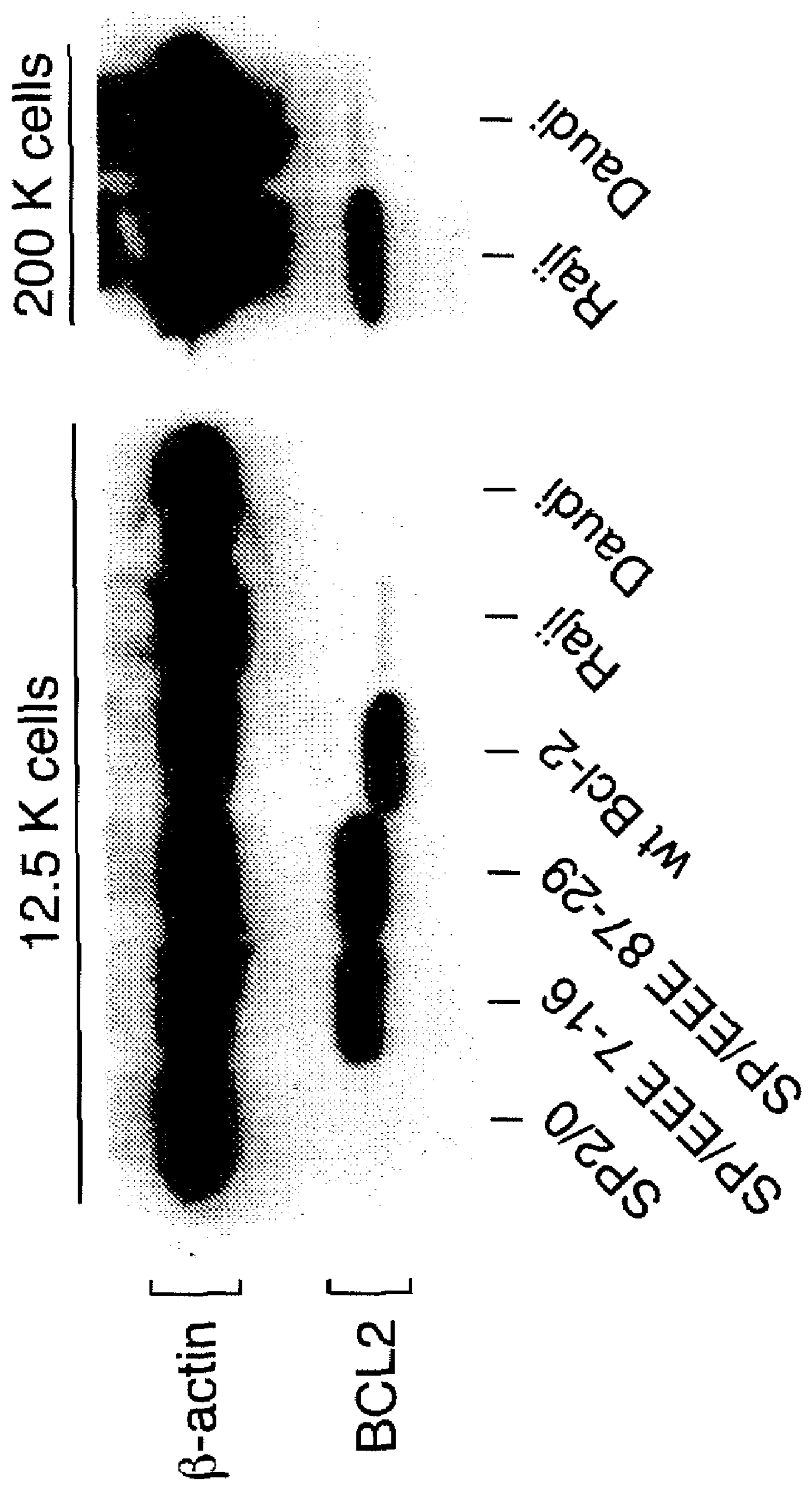
Figure 3C:
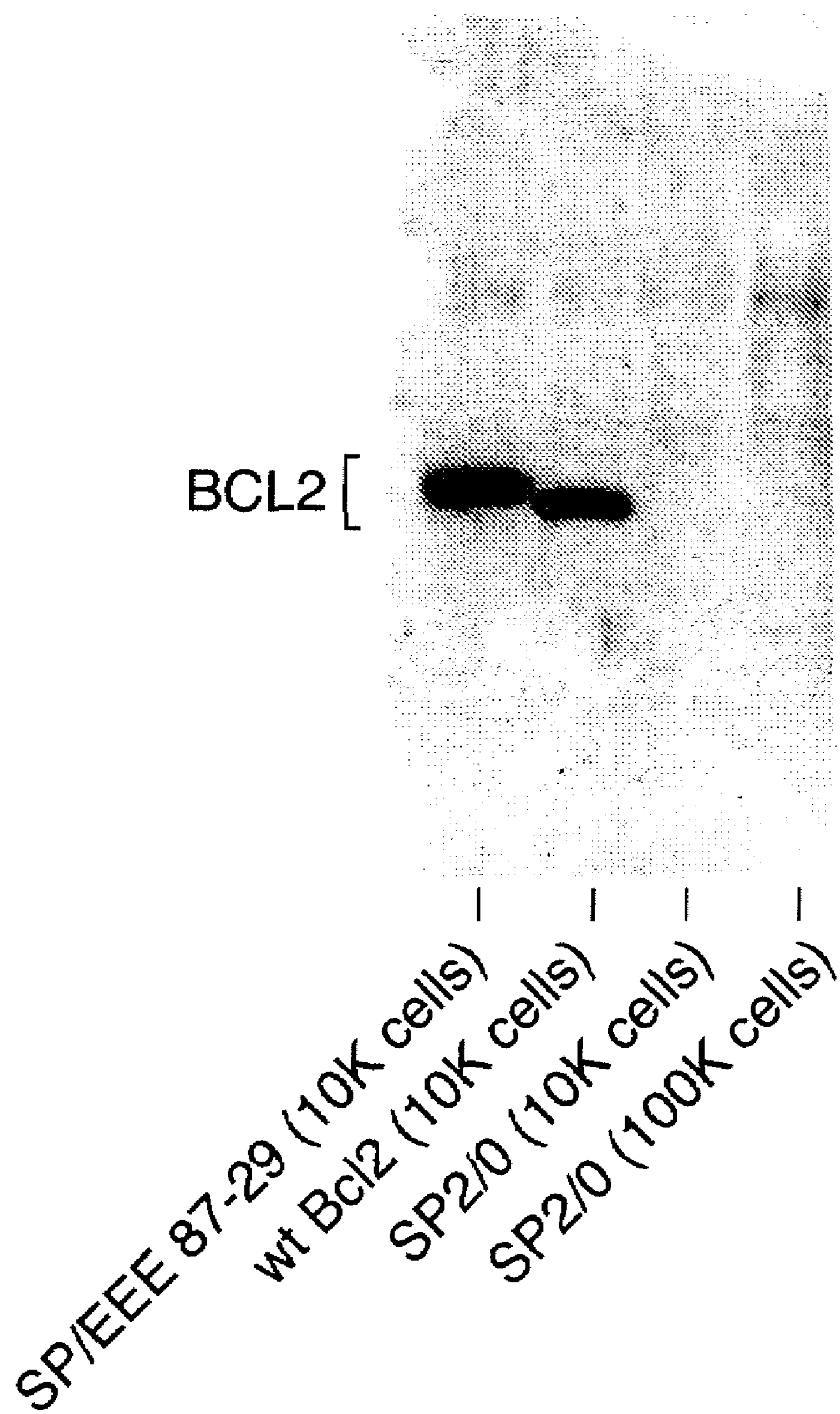

The level of Bcl-2-EEE expression in the new clones (shown for #87-29 and #7-16 in FIG. 3A) is about 20-fold higher than the endogenous level of Bcl-2 found in cell lines, such as Raji and Daudi. The parent Sp2/0 cells do not express Bcl-2. These observations were confirmed by anti-Bcl-2 immunoblot analysis with an anti-Bcl-2 mAb that recognizes mouse, rat, and human Bcl-2 (FIGS. 3B & 3C). We estimate that if there is any Bcl-2 expressed in Sp2/0 cells, it is at a level that is more than 2 orders of magnitude less than the Bcl-2-EEE in clone #87-29.

Figure 4:
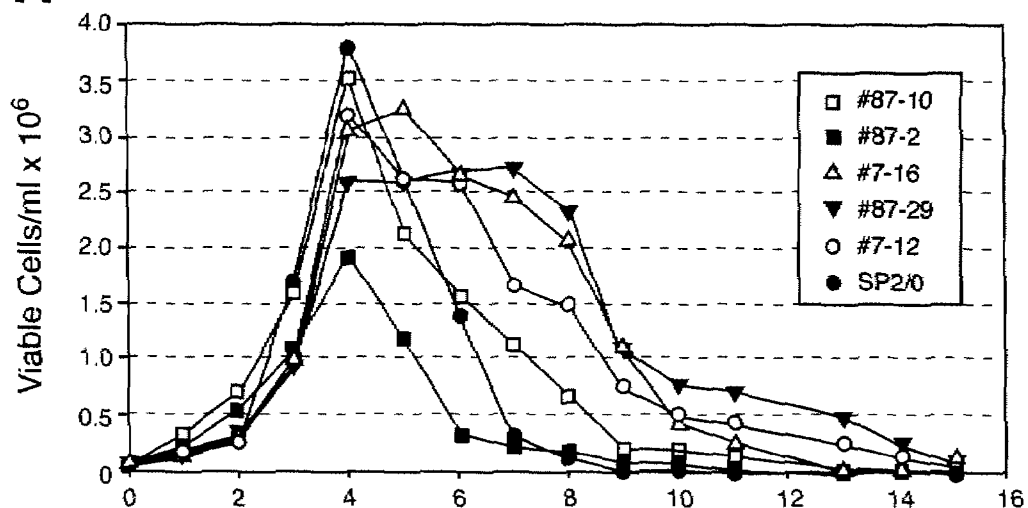
Figure 4:
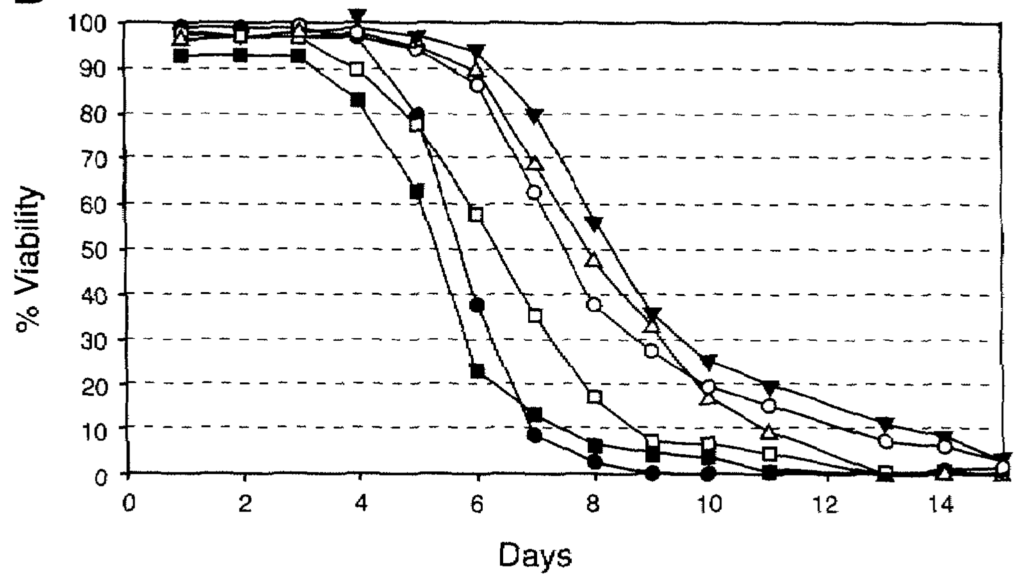

Growth curves were generated to compare the growth properties of five high-expressing Bcl-2-EEE subclones to Sp2/0 cells (FIG. 4). Four of the five subclones possess improved growth properties, achieving higher cell density and increased viability compared to Sp2/0. The two subclones (#87-29 and #7-16) showing superior survival were evaluated for growth and survival in low-serum or serum-free media.

Figure 5:
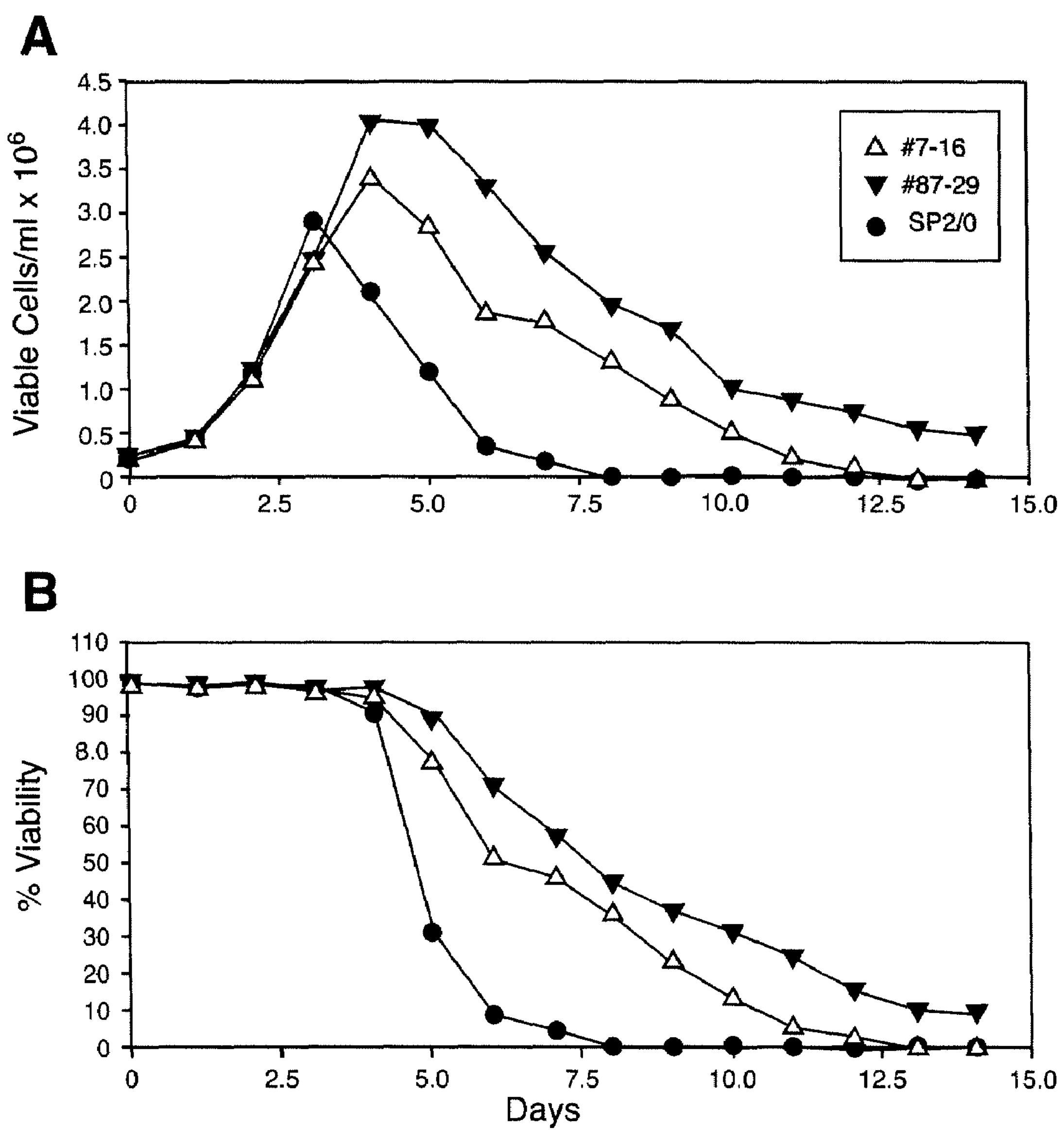
Figure 5:
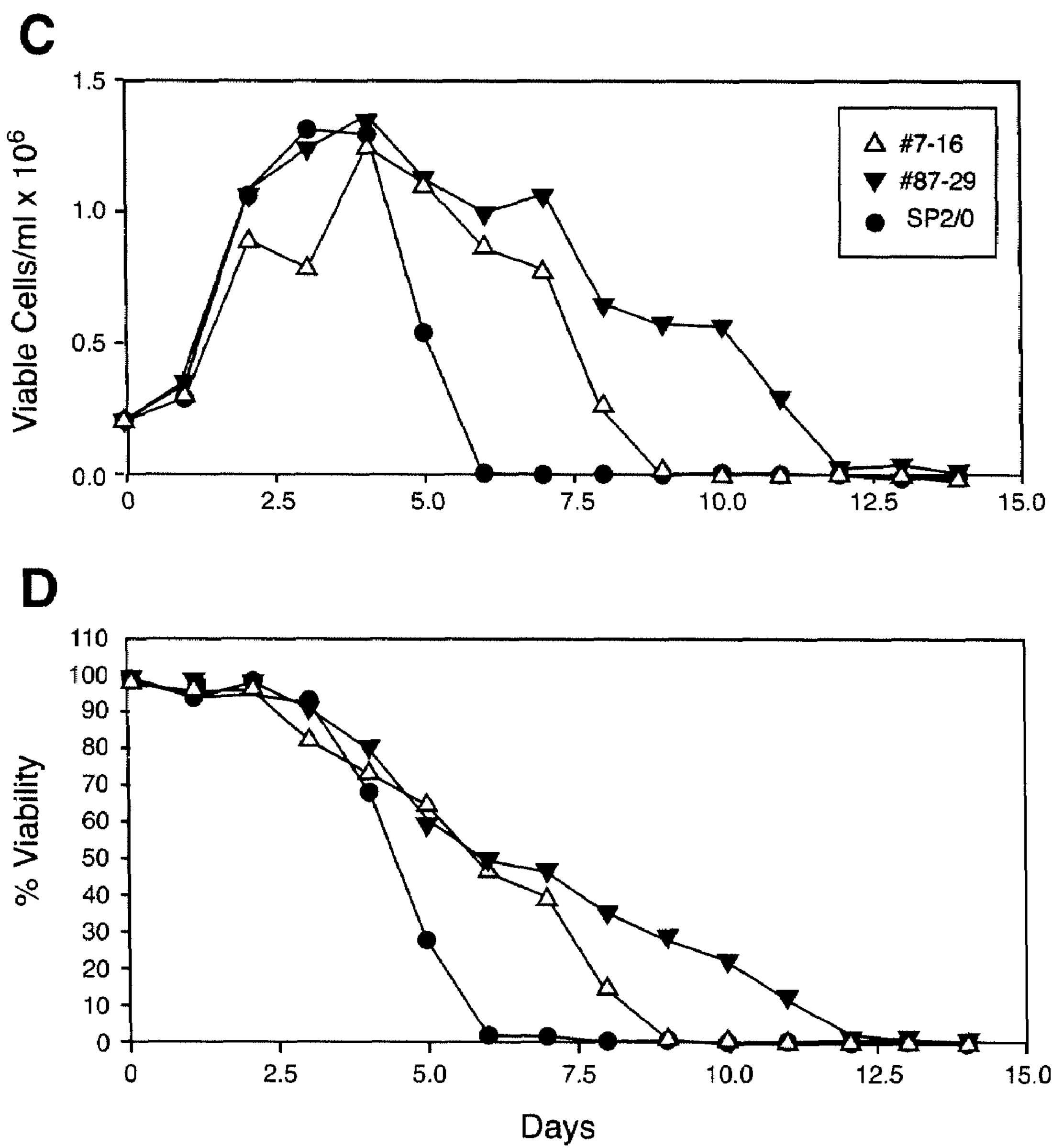
Figure 5:
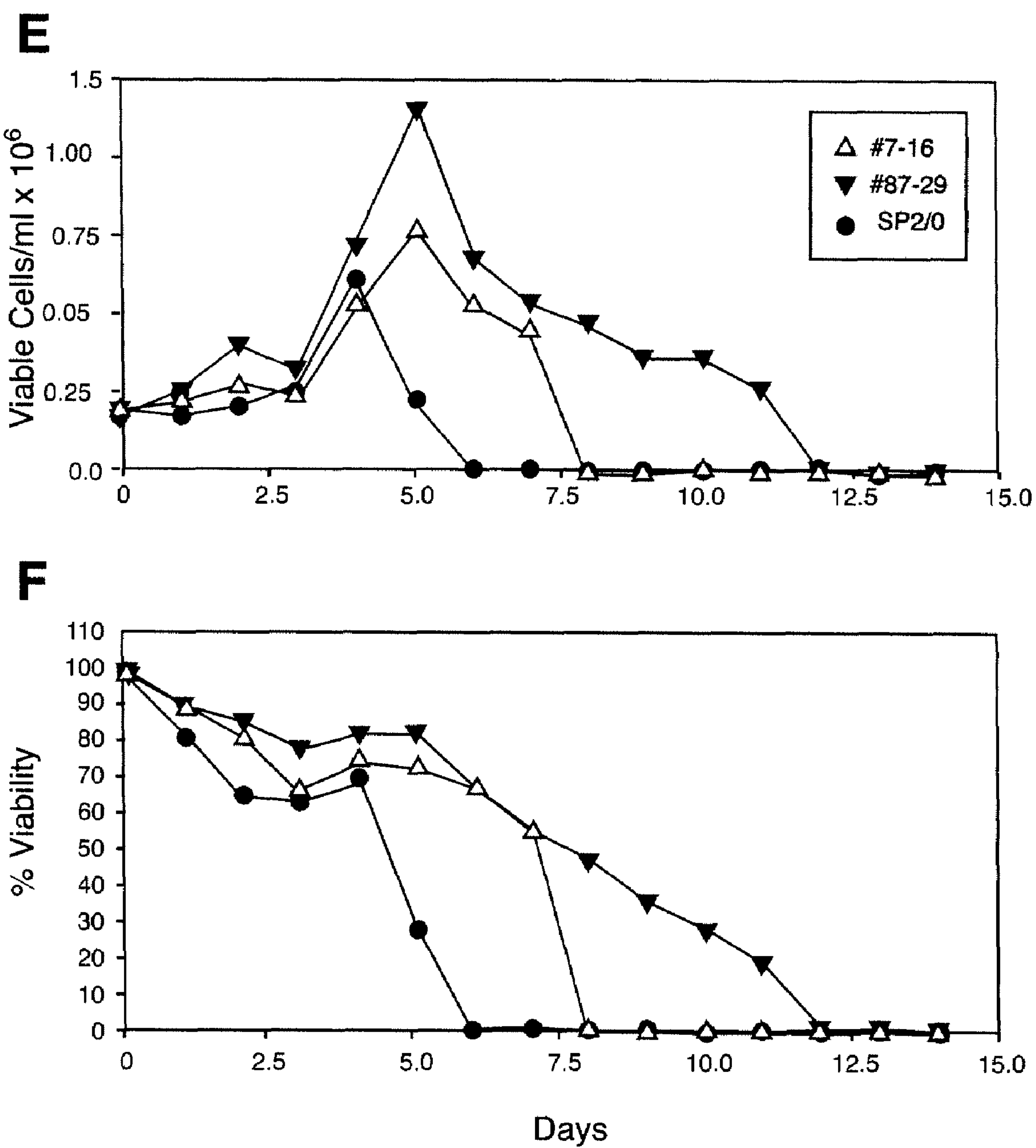

Cultures that were carried in 10% FBS were used to seed media supplemented with 10% FBS, 1% FBS or 0% FBS. In 10% FBS, subclone #87-29 grew to a high density and had more than 4 days increased survival compared to Sp2/0 cells (FIGS. 5A & 5B). In 1% FBS, all cells grew to approximately 35-40% of the density achieved in 10% FBS, with both subclones having a distinct survival advantage over Sp2/0 cells (FIGS. 5C & 5D). When transferred directly into serum-free media, the Sp2/0 cells only reached $6\times10^5$ cells/ml, while #87-29 grew to a two-fold higher density (FIG. 5E). In addition, #87-29 cells survived 4-6 days longer than Sp2/0 cells when cultured in serum-free medium (FIG. 5F). Because of its superior growth properties, #87-29 was selected for further development and referred to as SpEEE.

The methotrexate (MTX) sensitivity was determined for 87-29 (not shown). The data suggests that a minimum MTX concentration of 0.04 μM is sufficient for initial selection of MTX-resistant clones. Therefore, the same selection and amplification protocols used for Sp2/0 cells can be employed with the SP-EEE cells.

Bcl-2 is a pro-survival/anti-apoptotic protein. It has been demonstrated by several groups that a Bcl-2 deletion mutant missing the flexible loop domain (FLD) has an enhanced ability to inhibit apoptotosis (Figueroa et al., 2001, Biotechnology and Bioengineering, 73, 211-222; Chang et al., 1997, EMBO J., 16, 968-977). More recently, it was demonstrated that mutation of 1 to 3 S/T residues in the FLD of Bcl-2 to glutamic acid, which mimics phosphorylation, significantly enhances its anti-apoptotic ability (Deng et al. 2004, PNAS, 101, 153-158). The triple mutant (T69E, S70E and S87E) provided the most significant survival enhancement. Here, a similar Bcl-2 triple mutant construct (Bcl-2-EEE), was used to stably transfect Sp2/0 cells.

All the aforementioned experiments demonstrate that expression of Bcl-2-EEE reduces apoptosis rates in Sp2/0 cells. This effect was largely dose dependent, in that clones with higher expression levels survived longer than those with lower levels. The best clone, 87-29 (SpEEE), grows to a 15-20% higher cell density and survives an additional 4-6 days compared to untransfected Sp2/0 cells.

The Bcl-2-EEE level in clone SpEEE is approximately 20-fold higher than normal levels in Daudi or Raji cells. No Bcl-2 expression was detected in untransfected Sp2/0 cells. hMN-14-expressing Sp2/0 cells were transfected with a similar construct for expression of wild type Bcl-2 and a clone with exceptional growth properties and enhanced productivity was isolated. When this clone (664.B4) was amplified further with MTX, the Bcl-2 levels increased significantly. Ultimately, the amplified (3 μM MTX) cell line was subcloned and the Bcl-2 level of one clone (664.B4.1C1) was two-fold higher than 664.B4. This particular subclone has superior productivity and growth properties. The Bcl-2-EEE level in SpEEE is approximately two-fold higher than the level of Bcl-2 in the amplified 664.B4.1C1. SpEEE cells have a growth rate that is comparable to that of Sp2/0 cells and can apparently continue to grow for one additional day and reach a maximal density that is 15-20% higher than Sp2/0. A similar property was found for the E6/E7 expressing Sp-E26 cell line. The Bcl-2-EEE expressing SpEEE clone, which provides an additional 4-6 days survival over the parental Sp2/0 cells, is superior to the Sp-E26 clone, which only survives one additional day.

The SpEEE cell line as represented by the 87-29 clone is useful as an apoptosis-resistant host for expressing a recombinant protein upon transfection with a suitable vector containing the gene for that recombinant protein. In order for this cell line to be useful it must maintain its Bcl-2-EEE expression and survival advantage following transfection and amplification and during extended culture. It is unlikely that the stably transfected Bcl-2-EEE gene will be lost during subsequent transfection and therefore the survival properties should not diminish. It is possible that MTX amplification could even improve the survival of producing clones via increasing expression of Bcl-2 proteins. Indeed, this was the case with the hMN-14 664.B4 cell line, which was transfected with wild type Bcl-2. Following amplification and sub-cloning, the Bcl-2 level increased several fold and cell survival improved significantly.

The final SpEEE clone (#87-29) has a growth rate that is comparable to the parental Sp2/0 cells. However, the SpEEE 87-29 cells continue to grow for one additional day, reach a maximal density that is 15-20% greater and display an additional 4-6 days survival compared to Sp2/0. Further, the SpEEE cell line was considerably more tolerant to serum deprivation compared to Sp2/0 cells.

Example 7

SpEEE Based Cell Line Stability

The SpEEE-based cell lines were developed to enhance the growth and survival of the resulting transfectants. In order for this cell line to be useful it must maintain its Bcl-2-EEE expression and survival advantage following transfection and amplification and during extended culture without the selection agent, zeocin. To determine the stability of the Bcl-2 gene, several cell lines at different stages of development were analyzed by Guava Express for intracellular Bcl-2 expression.

Cells were counted using Guava ViaCount reagent and Guava PCA instrumentation (Guava Technologies, Inc). Approximately $1\times10^6$ cells were pelleted, and washed 2 times with PBS. FCM Fixation buffer (Santa Cruz Biotechnology, Inc., Santa Cruz, Calif.) was diluted 1:10 in PBS and 600 μl added to the cell pellet and incubated on ice for 15 minutes. Cells were washed 2 times with PBS and 0.5 ml of FCM Permeabilization buffer (Santa Cruz Biotechnology, Inc.) was added drop-wise to the cell pellet, which was incubated on ice for 15 minutes. Cells were washed twice and resuspended in 100 μl of FCM wash buffer (Santa Cruz Biotechnology, Inc.). Cells were then stained with 10 μl of phycoerythrin (PE)-conjugated mouse anti-human Bcl-2 antibody (Santa Cruz Biotechnology, Inc.), and incubated in the dark for 1 hour. Cells were washed twice and resuspended in 600 μl of FCM wash buffer. Stained cells were then analyzed with Guava Express software and Guava PCA instrumentation (Guava Technologies, Inc.).

Whole cell lysates from a known amount of cells were resolved by SDS-PAGE using 4-10% polyacrylamide gels. Proteins were electrophoretically transferred to a polyvinylidene fluoride (PVDF) membrane. The membrane was blocked with a solution containing 5% milk, 0.05% Tween in PBS. After blocking, the membrane was incubated in a solution containing either mouse anti-human Bcl-2 or mouse anti-rat, mouse and human Bcl-2 (Santa Cruz Biotechnology, Inc.). After washing with PBS containing 0.05% Tween (PBS-T), the membrane was incubated for 1 hour in peroxidase-conjugated anti-mouse IgG diluted 1:500 in 1% PBS-T (1% BSA in PBS containing 0.025% Tween 20) and washed again with PBS-T. The membrane was developed using LumiGLO Peroxidase Chemiluminescent Substrate Kit (KPL Protein Research Products, Gaithersburg, Md.) and visualized using Kodak Image Station 4000R (Eastman Kodak Company, Rochester, N.Y.).

Figure 10:
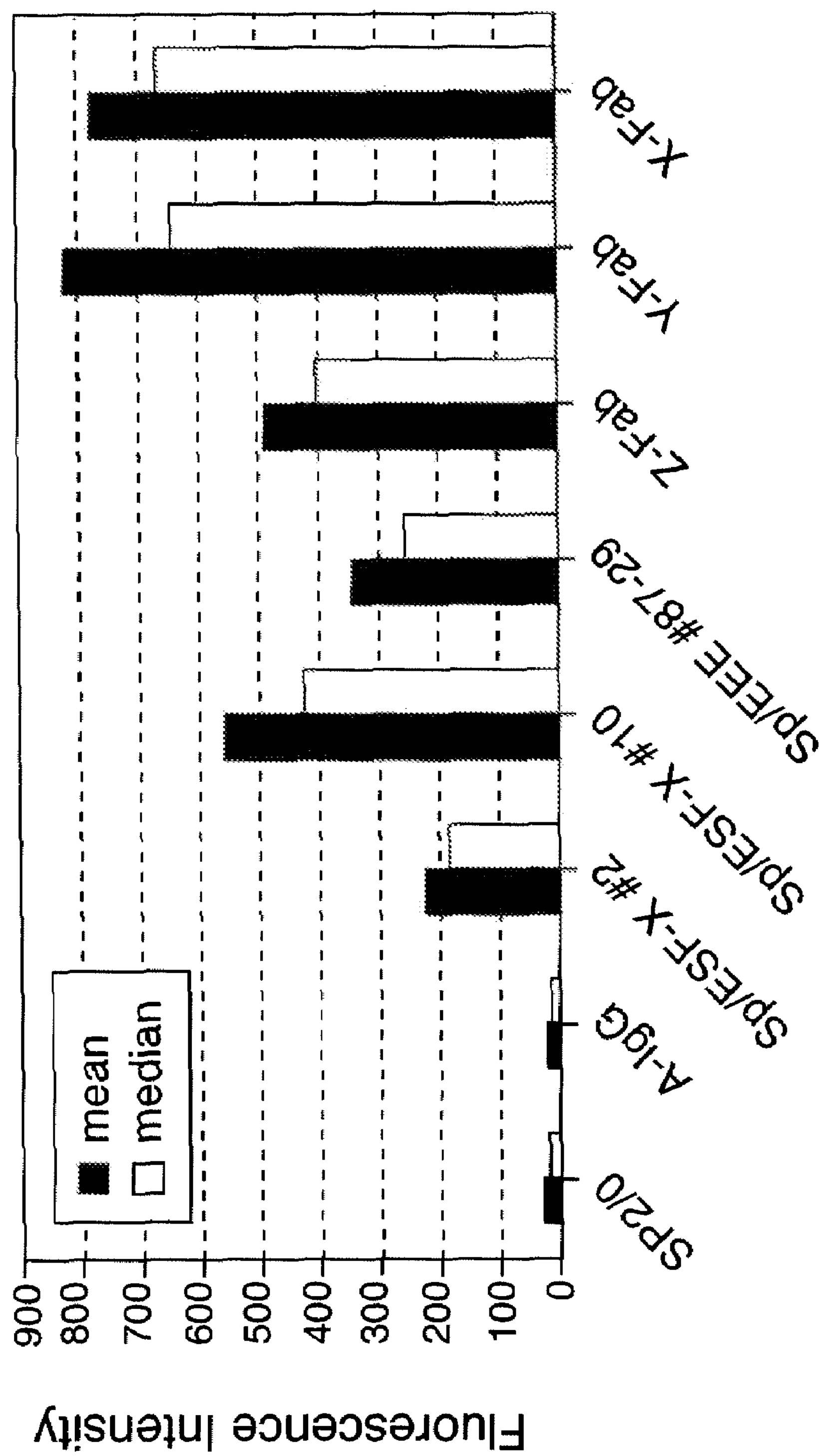

As shown in FIG. 10, Sp2/0 and A-IgG, which is an IgG-expressing Sp2/0 cell line, were negative for Bcl-2. Production of SpEEE by transformation with Bcl-2-EEE is described above. Two derivative cell lines, SpESF and SpESF-X are described in the following Examples. Three of the Bcl-2-EEE transfected cell lines, SpESF-X2, SpESF-X10 and SpEEE, which have been continuously cultured in media containing zeocin, were positive for Bcl-2-EEE expression. Three different Fab-expressing SpESF cell lines that were grown in the absence of zeocin for over 50 passages were found to express Bcl-2-EEE at levels even higher than those found for the parental cell lines, which suggests that the Bcl-2-EEE transgene may be co-amplified with the recombinant protein.

Example 8

Improved Production of Recombinant Proteins with the SpEEE Cell Line

There are two paths that can be taken when developing a cell line with enhanced survival for production of recombinant proteins. One method, which has been accomplished quite successfully, involves stable transfection of an already producing cell line with a pro-survival gene, such as Bcl-2. However, this method requires additional transfection, selection and cloning steps, thereby lengthening the cell line development process by at least two months and possibly much more. Further, screening for the "best" clone is rather involved, since a number of parameters need to be determined for each clone, including growth/survival, Bcl-2 expression level and productivity. Thus, only a small number of clones can be evaluated. It is quite possible that clones with the highest productivity may not have superior survival and vice versa. An alternative strategy, employed here, is to develop a parental cell line with superior growth and survival properties, which is subsequently transfected with the expression vector for production of the desired protein.

Compared to Sp2/0 cells, the SpEEE cells continue to grow for one additional day, reach a maximal density that is 15-20% higher, and survive an additional 4-6 days in culture. The cells retain their enhanced growth and survival properties when subsequently transfected with genes for the production of recombinant proteins, such as IgG, antibody fragments and fusion proteins, growth factors, such as G-CSF, GM-CSF, EPO (erythropoietin), EGF (epidermal growth factor), VEGF (vascular endothelial growth factor), cytokines, such as an interleukin family member (IL-1-IL-31), or interferon family members (such as alpha, beta or gamma interferon), oligonucleotides, peptides, hormones, enzymes, or vaccines (e.g., Hepatitis A, B or C, as well as others described above).

A DNA vector, such as pdHL2, containing one or more expression cassettes for recombinant protein(s), such as an IgG, is used to transfect SpEEE cells by standard methods, such as electroporation. The transfectants are plated in 96-well plates and clones are analyzed for protein production by established techniques such as ELISA or Biacore. Productive clones are subjected to increasing concentrations of MTX in the culture media over several months to amplify the genetic copy number. Since the Bcl-2-EEE-expressing clones grow to about 20% higher cell density and survive at least an additional 4 days as compared to clones generated in Bcl-2 negative Sp2/0 cells, the former will produce at least 20% more recombinant protein in standard flask or roller bottle culture. An even greater increase is realized in suspension, perfusion or fed-batch bioreactor cultures.

Example 9

Improved Ab-Production of Bcl-2 Transfected Clones Cultivated in a Bioreactor

Both 665.2B9#4 and the parent clone 665.2B9 of Example 5 were weaned into serum-free media. The cells were adapted to a customized formulation of hybridoma serum-free medium (HSFM) (Immunomedics PN 10070) containing 3 μM MTX by continuous subculture in T-flasks for several months. The adapted cells were scaled up from T-flasks to roller bottles for banking. A master cell bank (MCB) for each cell line was created with $1\times10^7$ viable cells in each 1-mL vial using an FBS-free cryopreservation solution composed of 45% conditioned medium (medium that is collected as supernatant after centrifugation of a culture in the exponential growth phase), 10% DMSO and 45% HSFM. The MCB cell lines were designated 665.2B9.1E4 (without Bcl-2 gene) and 665.B4.1C1 (with Bcl-2 gene), respectively. The growth properties and antibody production of these two clones were compared under batch culture conditions.

Experiments were conducted in 3-L bench-scale bioreactors using the above cells expanded from the MCB. The 3-L bioreactor system is the scale-down model of a 2500-L cGMP bioreactor system. Therefore, the evaluation results would support the suitability of these cell lines for large-scale commercial manufacturing.

The same growth HSFM as that used in creating the MCB (Immunomedics PN 10070) was used to maintain the cell line and prepare the inoculum. Basal HSFM, a customized formulation based on the growth HSFM with customized modifications (Immunomedics PN 10194), was used in the 3-L fed-batch bioreactor process. Both media contain insulin and transferrin as the only trace proteins. Additional 0.1% Pluronic F68 was incorporated into the formulation to protect cells from shear caused by agitation and aeration. This media also contained 3 μM MTX.

The fed-batch experiments were conducted in 3 L Bellco spinner-flask bioreactor systems (Bellco glasses, Vineland, N.J.) with 2 L of working volume. The bioreactor temperature, pH and dissolved oxygen (DO) were monitored and controlled by single loop controllers. The reactor temperature was controlled at 37° C. by a heating blanket. The culture pH was controlled at 7.3 by the addition of $CO_2$ or 6% $Na_2CO_3$. Aeration was performed through a cylindrical sintered sparger at 10 ml/min. DO was controlled above 40% of air saturation by intermittent sparging of $O_2$ into the medium. A constant agitation rate of 50 about 60 rpm was used throughout the cultivation.

A frozen vial from MCB was thawed and recovered in T-flasks in approximately 1 to 2 weeks. The cells were then expanded from T-flasks to roller bottles prior to inoculation into the bioreactors. Cells were cultured at 37° C. in a 5% $CO_2$ atmosphere and maintained in the exponential growth phase throughout the expansion process.

Prior to the inoculation, 1.2 liters of Basal HSFM was pump-transferred into the bioreactor aseptically. The medium was air saturated to calibrate the dissolved oxygen (DO) probe. A medium sample was also taken to calibrate the pH probe. Once pH probes and DO probes were calibrated, both controllers were set to AUTO modes. Once the system reached set points of pH (7.3) and temperature (37° C.), calculated amount of inoculum from roller bottle was pump transferred into the bioreactor. The post-inoculation viable cell density (VCD) was around 2×10.sup.5 vial cells/ml.

The feeding strategy is as follows. During the cultivation, concentrated nutrient solutions were fed into the bioreactor to provide the cells with necessary and non-excessive nutrients. Concentrated nutrient solutions were delivered to the culture via continuous feeding and pulse feeding. The continuous feeding solutions were pump transferred into the reactor continuously using peristaltic pumps (Watson-Marlow 101U/R). The pulse feeding solutions were pulse fed once a day into the culture.

During the cultivation, bioreactor samples were taken periodically for off-line analysis. The viable cell density (VCD) and the cell viability were measured by microscopic counting using a hemocytometer after staining with 0.4% trypan blue dye. The glucose, lactate, glutamine, ammonia concentrations were measured using a Nova Bioprofile 200. The antibody concentration was determined by HPLC using a protein A affinity chromatography column (Applied Biosystems, P/N 2-1001-00).

The specific antibody productivity was calculated by dividing the cumulative antibody produced by the time integral of the total viable cell in the culture:

$$Q_{[MAb]} = \frac{([Mab]_{t1} \cdot V_{t1} - [Mab]_{t0} \cdot V_{t0}}{\int_0^{t1} VCD - V\, dt},$$

in which $\int_0^{t1}$VCD·Vdt is approximated by the $$\text{Trapezium Rule: } \frac{(VCD_{t0} \cdot V_{t0} + VCD_{t1} \cdot V_{t1})(t1 - t0)}{2}$$

As compared to 665.2B9.1E4 cells, 665.B4.1C1 cells exhibited much better growth (not shown). The antibody yields of two cell lines were also compared. The final yield of 665.2B9.1E4 cells was 0.42 g/L in one culture process and 0.55 g/L in a second culture process. For comparison, 665.B4.1C1 cells delivered a higher final yield of 1.5 g/L in both processes.

The daily specific antibody productivities (per cell basis) were calculated and the 665.2B9.1E4 cells had an average daily $Q_{[MAb]}$ of approximately 15 pg/cell/day throughout the course of cultivation for both processes. The 665.B4.1C1 cells showed a daily Q[MAb] between about 20 to 25 pg/cell/day until day 9. Thereafter the productivity declined.

Compared with the 665.2B9.1E4 cell line, the 665.B4.1C1 cell line exhibited a higher specific antibody productivity of about 25 pg/cell/day as compared to 15 pg/cell/day. Combining with its better growth, the 665.B4.1C1 cell line tripled the final antibody yield to 1.5 g/L as compared to 0.55 g/L achieved by the 665.2B9.1E4 cell line. These results demonstrate that transfection of Bcl-2 or its analogs, such as Bcl-2-EEE, into cell lines grown in serum-free media in a bioreactor modeled for large-scale commercial preparation of a recombinant protein, in this case an antibody for clinical use, show the same increase in protein production observed under batch cultivation.

Example 10

Development of SpESF Serum-Free Pre-Adapted Cell Line

Since the SpEEE cell line showed enhanced growth and survival properties as well as superior tolerance to serum deprivation, it was decided to explore the feasibility of developing an SpEEE cell line derivative that is pre-adapted to growth in serum-free media and to use this line for transfection, cloning and amplification. The following describes the development of the SpESF (SpEEE serum-free) cell line. Feasibility for production of cloned proteins, such as antibodies or fragments, was demonstrated by transfection with the C-AD2-Fab-h679-pdHL2 expression vector.

Adaptation to Growth in Serum-Free Media and Subcloning

Figure 6:
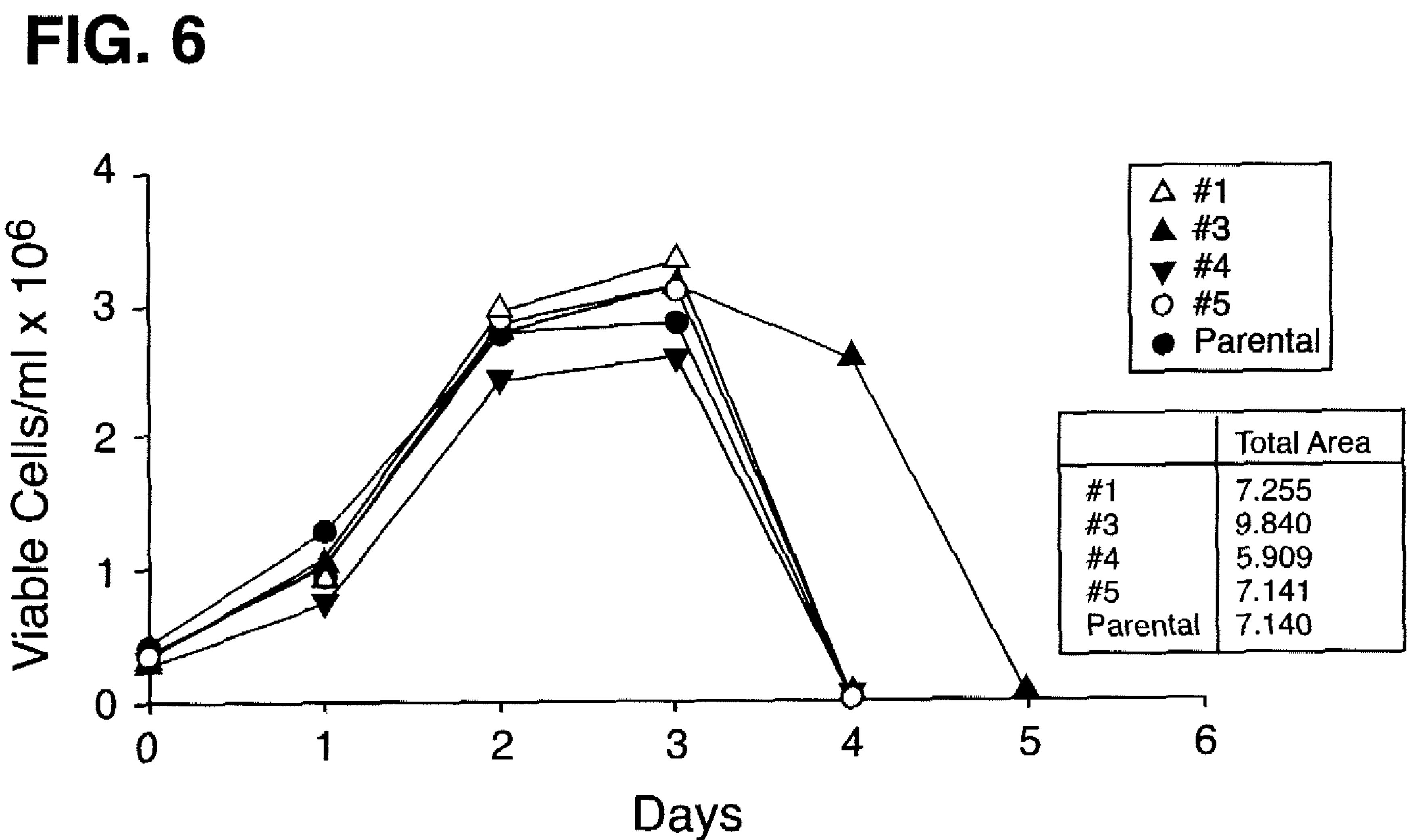

The enhanced survivability of SpEEE cells in serum-free media led to the successful development of the entirely serum-independent host cell line, SpESF. SpEEE cells were adapted to serum-free media over an 8-week period via step-wise reduction of serum from the media. Once the cell line was adapted to growth in serum-free media, a limiting dilution was performed to determine if the cells were capable of surviving at such low densities, as would be necessary for future transfections and subcloning. Seven subclones resulted from the limiting dilution and the growth properties of 4 of the 7 subclones were compared to those of the parental SpEEE cell line. FIG. 6 shows that subclone #3 survived for one additional day and gave an area under the curve (AUC) 38% greater than the parental Sp-EEE or other subclones. In addition, subclones #3 and #1 reached higher maximal cell density (3.2 to 3.3 million/mL) than the other clones (not shown). Since subclone #3 appeared to be better adapted to undergo successful transfection, it was selected for further development and designated as the SpESF cell line.

Figure 7A:
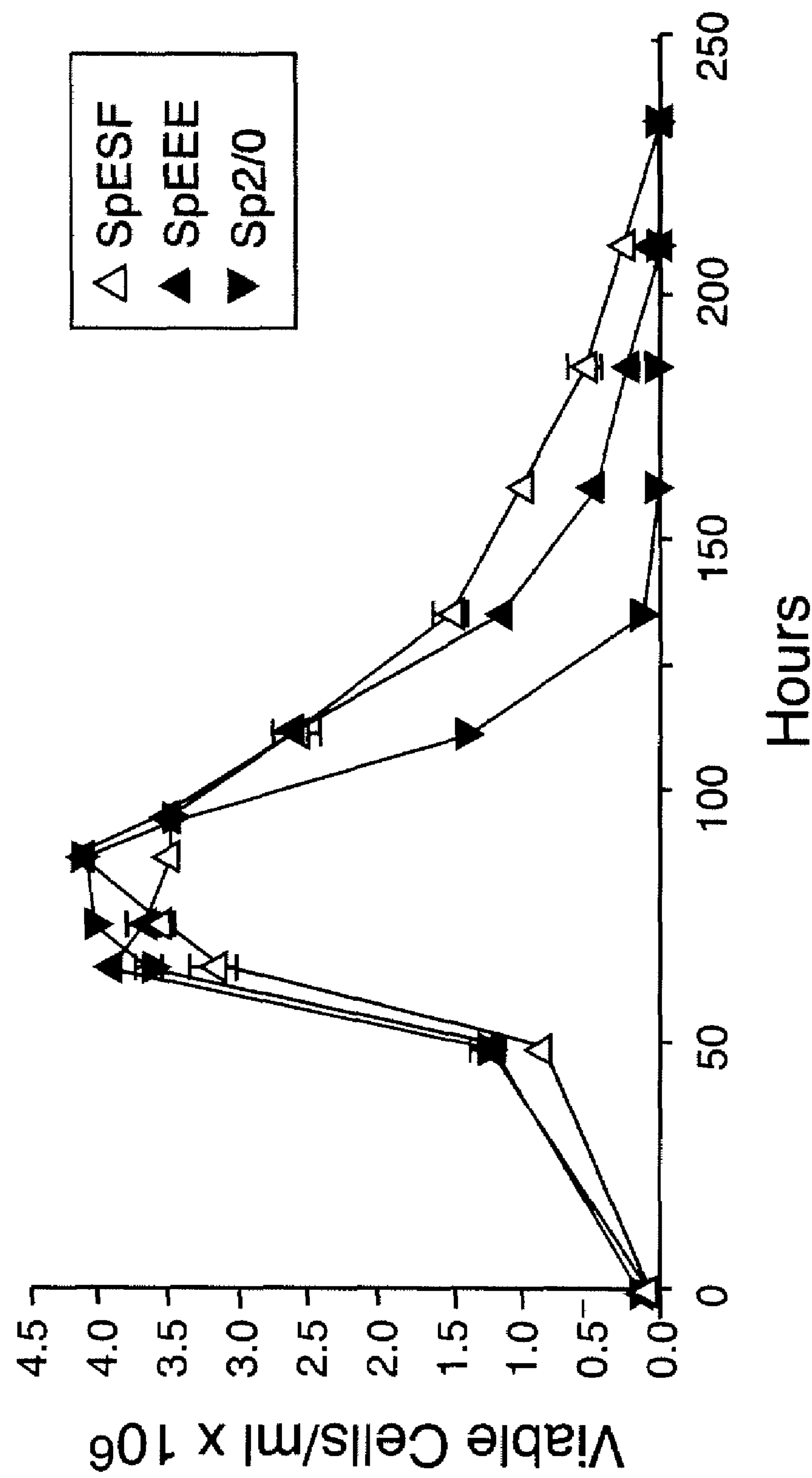
Figure 7B:
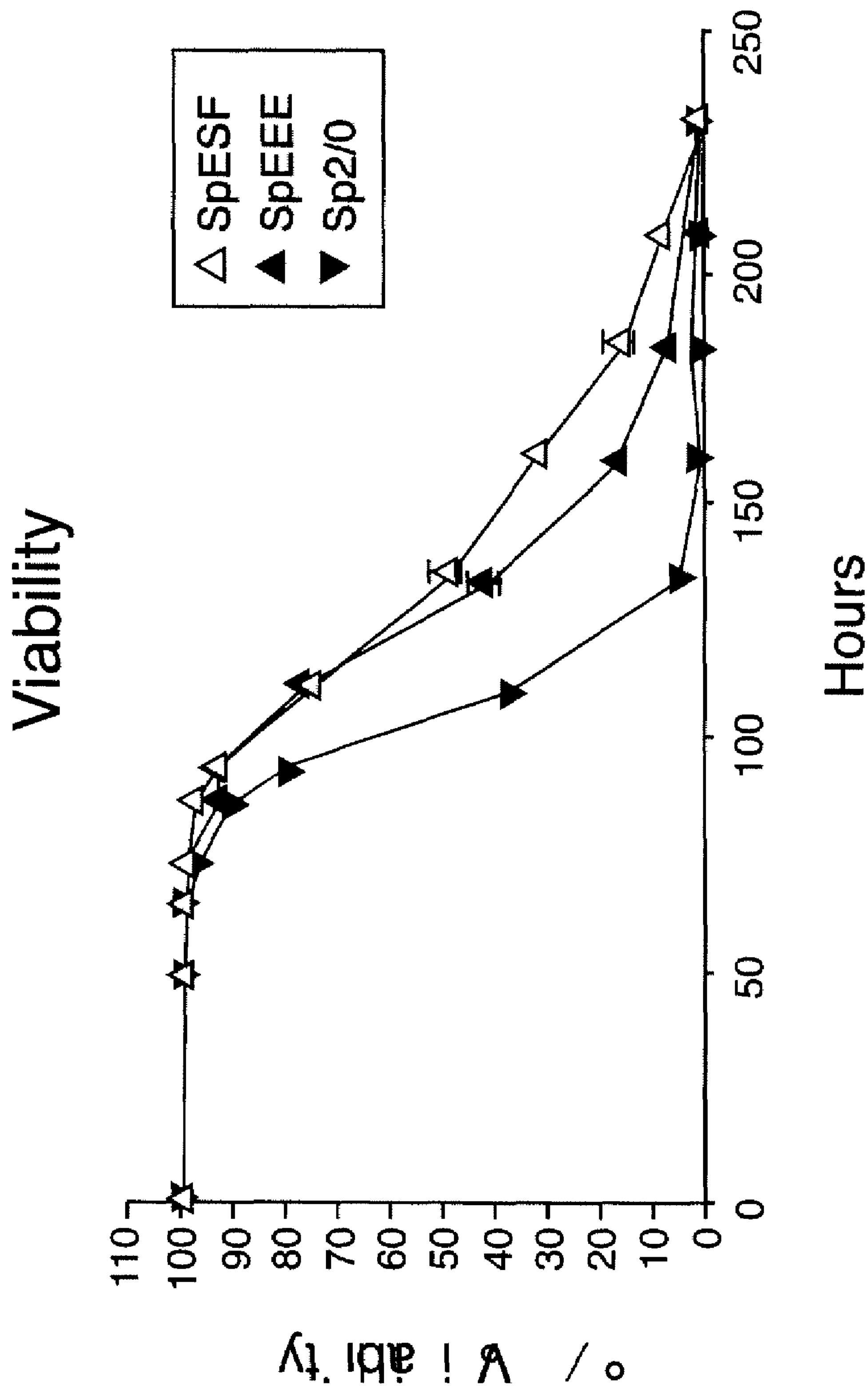
Figure 8A:
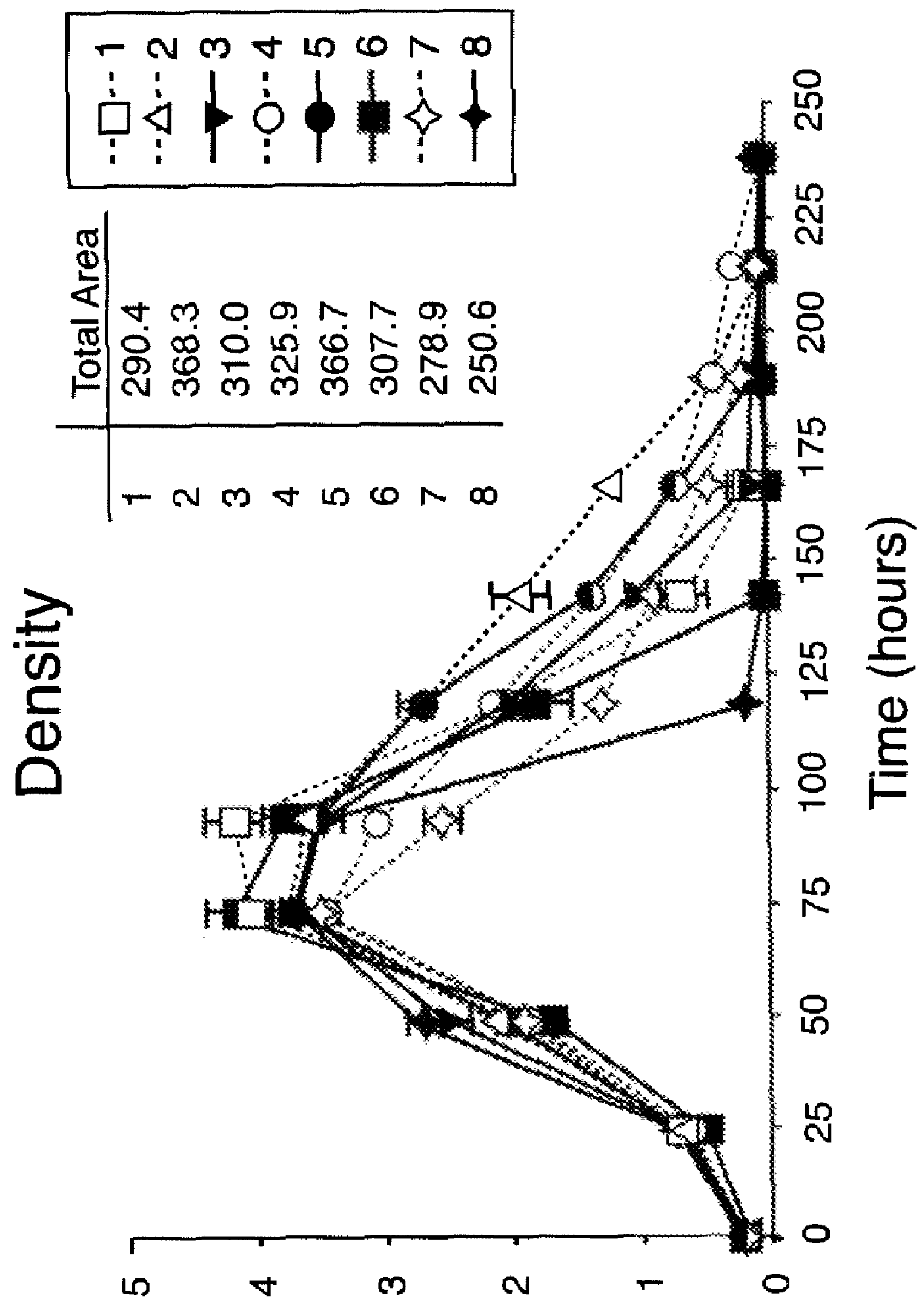
Figure 8B:
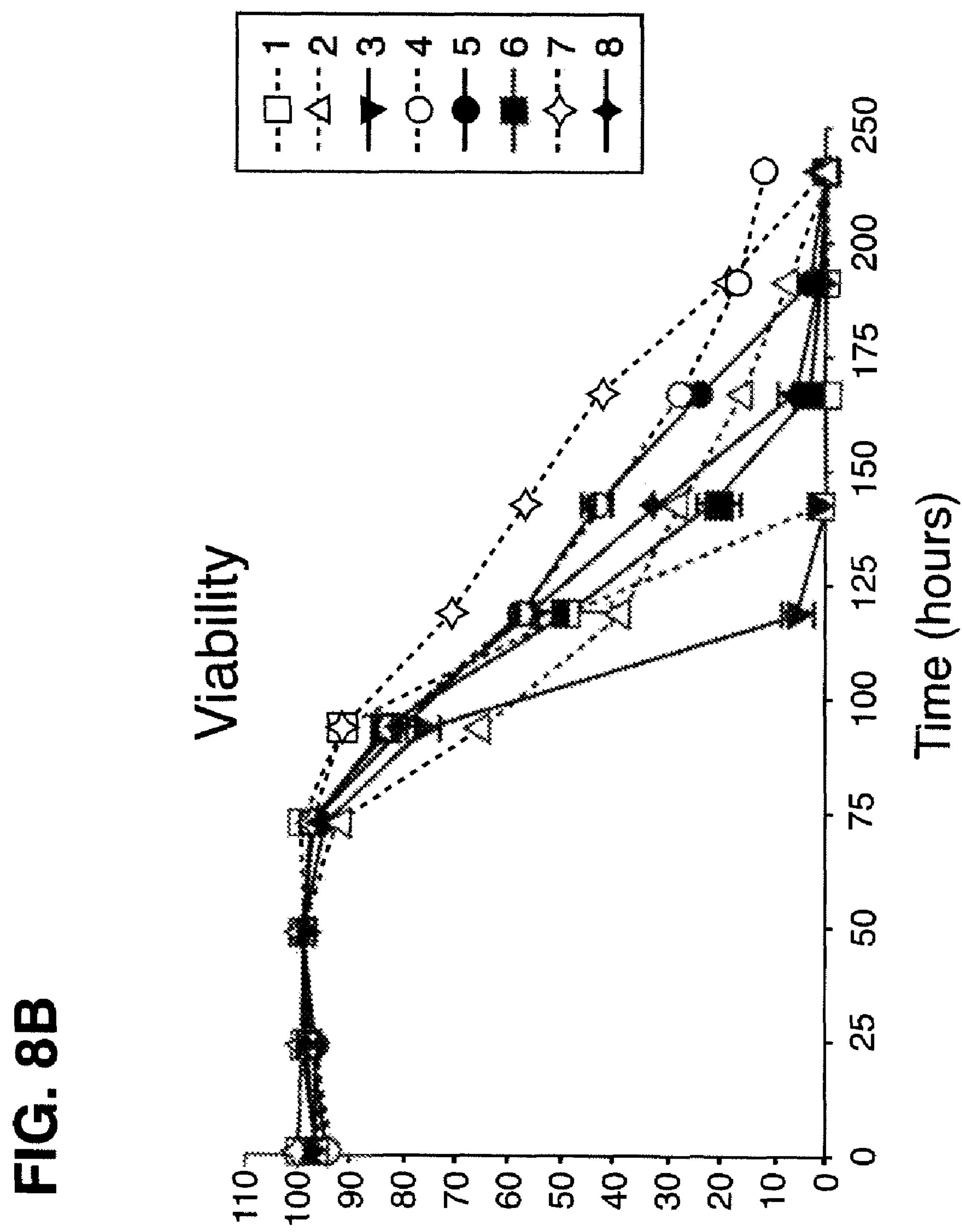
Figure 8C:
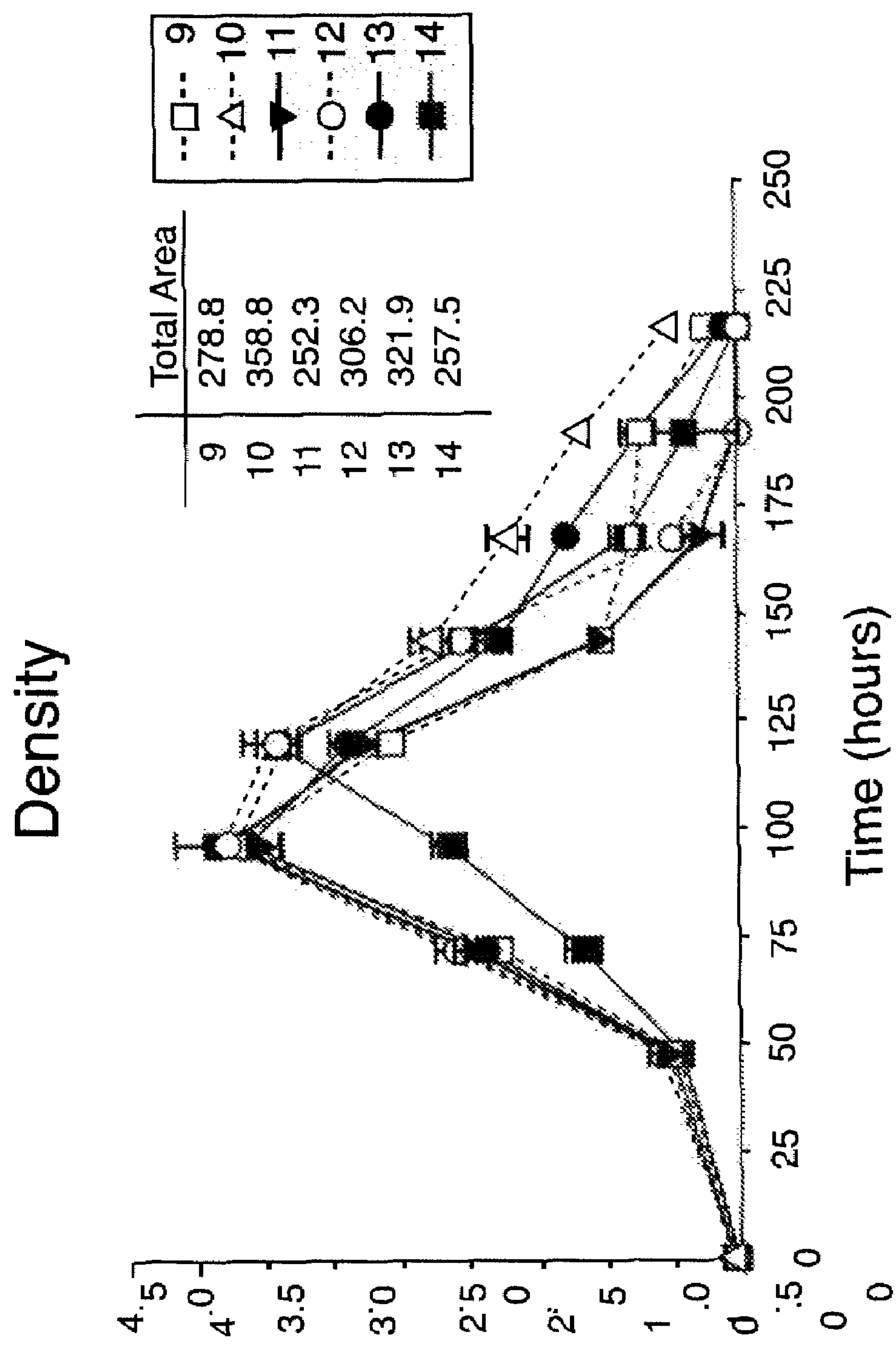
Figure 8D:
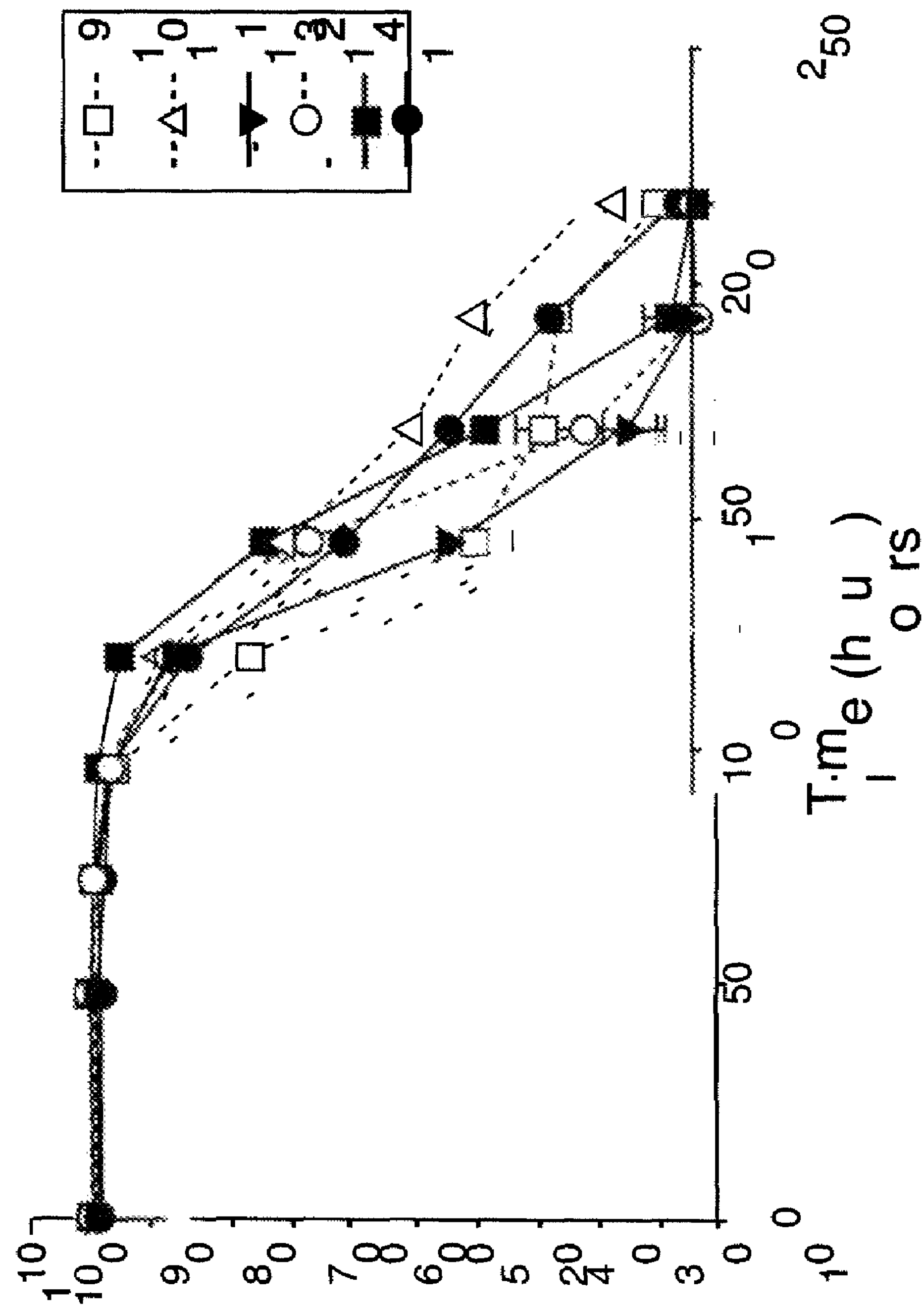

After several months of continuous culture and full adaptation of the SpESF cell line to growth in serum-free media, growth curves were compared to Sp2/0 and SpEEE in media supplemented with 10% FBS. FIG. 7 shows that the SpESF cell line grown in serum-free media is superior to Sp2/0 cells in 10% FBS, with the former surviving for an additional 3 days. Further, SpESF is equivalent or better than the SpEEE cell line (in 10% FBS) in terms of both maximum cell density and longevity.

Transfection of SpESF Cells with h679-AD2

Based on the above data SpESF cells (subclone #3) were transfected by electroporation with 30 μg of h679-AD2-pdHL2. After 48 hours cells were selected with 0.1 μM MTX. As a control, SpEEE cells in 10% FBS were also transfected with h679-AD2-pdHL2 by electroporation under the same conditions. After 10 days plates were ready for screening via ELISA using BSA-IMP-260 coated plates. For both transfections approximately 130 of 400 wells contained positive clones. Positive SpESF cells from wells with the 40 highest OD readings were transferred to 24-well plates and the MTX was increased to 0.2 μM MTX. After the cells in the 24-well plates reached terminal, further screening by BIACORE analysis using an HSG sensorchip was performed. Four of the screened clones had a productivity of >50 mg/L. The highest producing clone (h679-AD2-SF #T6) had an initial productivity of 82 mg/L. These initial productivity results were very similar to those obtained from a previous transfection of this construct using SpEEE cells in 10% FBS.

Amplification with MTX

The h679-AD2-SF# T6 clone was selected for MTX amplification. After 2 weeks the MTX concentration was increased from 0.2 μM to 0.4 μM. After only 2 MTX increases, some amplification in productivity can already be observed (Table 3).

TABLE 3

| MTX Concentration | Productivity |
|---|---|
| 0.1 μM MTX | 82 mg/L |
| 0.2 μM MTX | 93 mg/L |
| 0.4 μM MTX | 103 mg/L |

Conclusions

The data presented above for SpESF indicate that transfection, cloning by limiting dilution and MTX amplification can all be accomplished under serum-free conditions in less than a month. This was demonstrated with the transfection of the h679-Fab-AD2-pdHL2 expression vector, resulting in the initial very high production of 82 mg/L, which could be amplified to 103 mg/L in two weeks. Further amplification is expected with a longer time of MTX exposure. The initial productivity of the best clone (T6) of 82 mg/L surpasses the initial productivity of the best h679-AD2-pdHL2 clone (5D8) from the original transfection of the parent SpEEE cell line carried out in 10% FBS, which was around 50 mg/L. SpESF cells have also been transfected with EPO-DDD2-pdHL2 for production of erythropoietin.

As shown in Table 4, which compares the key parameters of SpESF with those of the existing PER.C6 cell line (Jones et al in Biotechnol. Prog. 2003, 19: 163-168), Sp/ESP is superior to PER.C6 in many categories.

TABLE 4

| | | Sp/ESP | PER.C6 |
|---|---|---|---|
| Parental Cell line | | Mouse myeloma | Human embryonic retina + E1 |
| Anti-apoptotic gene | | Bcl-2-EEE | None |
| Transfection | Method | Electroporation | Lipofectamine |
| | Efficiency | 130/400 | ? |
| | Growth | Suspension | Adherent |
| | Medium | SFM | 10% FBS |
| Screening | Growth | Suspension | Adherent |
| | Medium | SFM | 10% FBS |
| Selected clones | Growth | Suspension | Suspension |
| | Medium | SFM | SFM |
| | Adaption time | None | 4 weeks |
| Doubling time | | ~12 h | 30-33 h |
| Cell culture | Vessel | T-25 | Roller bottle |
| | Medium | SFM | SFM |
| | Maximal density | $3.3 \times 10^6$/mL | $5 \times 10^6$/mL |
| | Productivity | 103 mg/L of Fab* | 300-500 mg/L of IgG |

*Equivalent to 300 mg/L of IgG

Example 11

Use of SpESF for Protein Production

The approximately 11-Kb plasmid vector, pdHL2, used for high-level expression of humanized mAb in myeloma cell lines has been described previously (Gillies et al., 1989, J Immunol Methods 125:191-202; Qu et al., 2005, Methods 36:84-95). The vector contains expression cassettes for IgG heavy and light chains under transcriptional control of the MT1 promoter and the dhfr gene, which encodes dihydrofolate reductase conferring resistance to methotrexate (MTX) for selection of transfected clones and gene amplification for improved protein expression.

A-IgG-pdHL2 and X, Y, or Z-Fab-pdHL2 (where A, X, Y and Z represent four different humanized antibodies) were transfected into SpESF cells via electroporation. Plasmid DNA (20-30 μg) was linearized with SalI, added to SpESF cells and pulsed twice at 450 volts, 25 μF using a Gene Pulser (BioRad Laboratories, Inc., Hercules, Calif.). Cells were resuspended in 80 ml of 0% H-SFM and plated onto eight 96-well tissue culture plates. After 48 hours, selection media containing MTX was added to each well. Screening of MTX-resistant clones was performed 1-2 weeks later via sandwich ELISA to select high-level antibody-expressing clones. Selected clones were then transferred to 24-well tissue culture plates for further testing and expansion.

For transfected cells expressing antibodies, antibody expression was determined by sandwich ELISA using mouse anti-human IgG kappa chain (SouthernBiotech, Birmingham, Ala.) coated on plates (Nalge Nunc, Rochester, N.Y.). Media supernatant fluid was diluted in 1% PBS-T and incubated in the ELISA plate for 1 hour at room temperature. The wells were then washed 3 times with PBS-T. Horseradish peroxidase (HRP)-conjugated goat anti-human IgG $(Fab')_2$ specific second antibody (Jackson ImmunoResearch Laboratories Inc., West Grove, Pa.) was added to the wells for 1 hour. The plate was washed 3 times and substrate solution containing 4 mM ortho-phenylenediamine (OPD, Sigma, St. Louis, Mo.) and 0.012% $H_2O_2$ in PBS was added to the wells and allowed to develop in the dark for approximately 15 minutes. The reaction was stopped with the addition of $4NH_2SO_4$ and plates were read at $OD_{490}$ using an EnVision plate reader (Perkin Elmer, Waltham, Mass.). An exemplary result for antibody production is shown in Table 5.

To date, more than 20 recombinant proteins have been produced in SpESF transfectants with the transfection, selection, amplification, and expression steps all carried out in serum-free medium. Moreover, following the same amplification protocols that have been used successfully for the parental Sp2/0 cells, we have shown similar amplification of recombinant protein expression upon increasing concentration of MTX. Table 5 summarizes the productivity of an IgG- and a Fab-expressing cell line derived from SpESF at each step of MTX amplification.

Typical productivity for an IgG upon complete amplification is 150-200 mg/ml in commercially available serum-free media in roller bottles grown in batch cultures, which is expected to increase with media optimization and fed-batch cultures.

TABLE 5

Amplification progress of 2 different constructs, A-IgG and Z-Fab. Productivity was evaluated by sandwich ELISA.

| A-IgG MTX (μM) | Productivity (mg/L) | Z-Fab MTX (μM) | Productivity (mg/L) |
|---|---|---|---|
| 0.1 | 50 | 0.2 | 89 |
| 0.4 | 102 | 0.8 | 84 |
| 0.7 | 128 | 1.5 | 97 |
| 1 | 133 | 3.0 | 127 |
| 2 | 177 | 4.5 | 141 |
| 3 | 189 | | |

Example 12

Transfection of SpESF with C-DDD2-Fab-hMN-14

Linearized C-DDD2-Fab-hMN-14-pdHL2 DNA (40 μg) was used to transfect $2.4\times10^6$ SpESF cells by electroporation using standard conditions. Cells were plated into sixteen 96-well plates and selected with 0.15 μM MTX. Approximately 1000 positive clones were identified, 32 of which were high-level producers. Some of the high producers were amplified with increasing MTX, resulting more than a two-fold increase in productivity. Following amplification, high producing cell lines were subcloned by limiting dilution at 0.3 cells/well in three 96-well plates resulting in sixty-two viable subclones representing survival efficiency of >70%.

Example 13

Development of SpESF-X Cells

Figure 9:
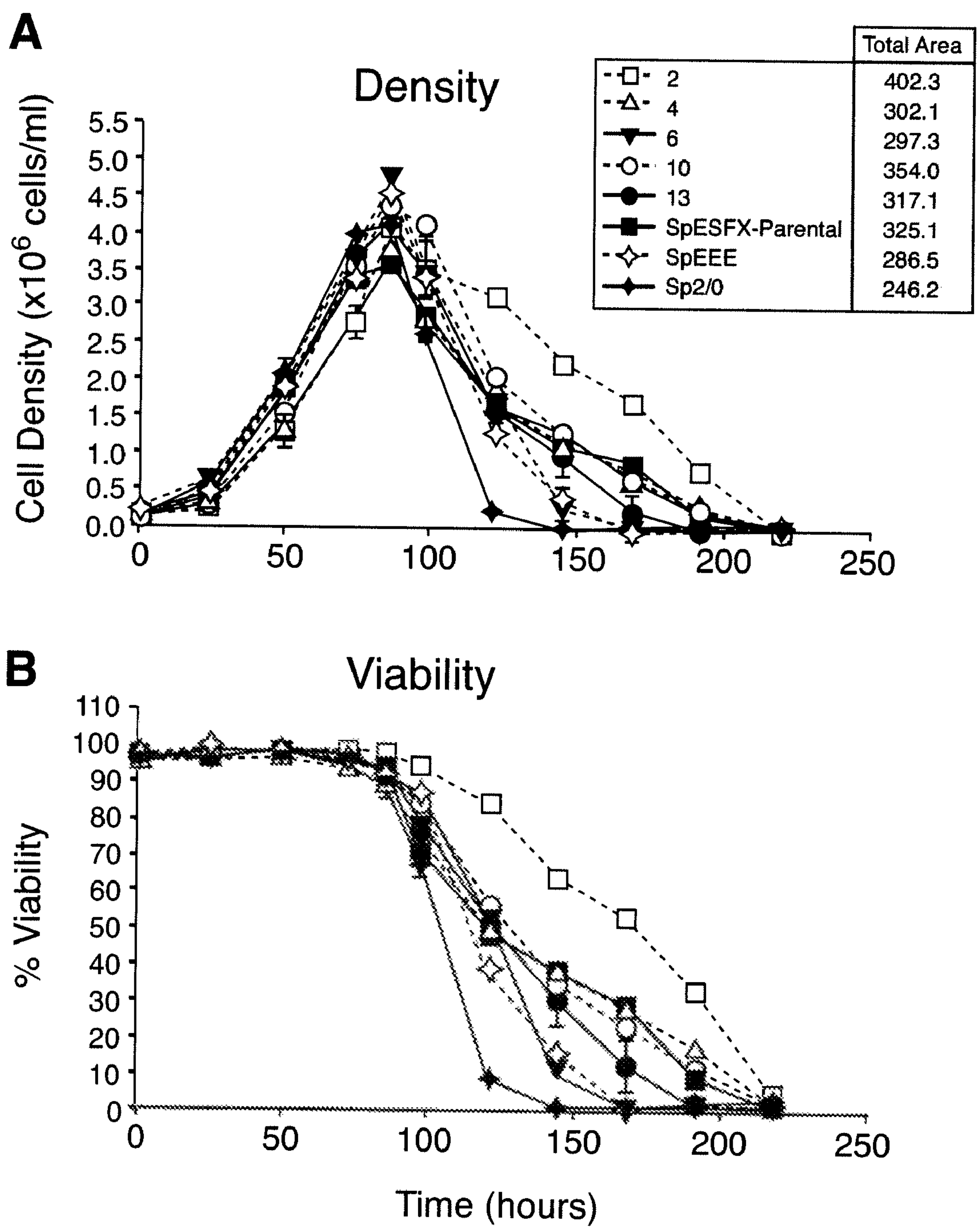

For further enhancement, the SpESF cells were subjected to iterative rounds of stressful growth conditions in the hope that even more robust cell lines could be obtained. SpESF cells were allowed to overgrow until the viability reached 50-75%. At this point the cells were allowed to recover in fresh media, followed by another typical passage in fresh media. This cycle was repeated over 4 months and then subcloning by limiting dilution was performed, which resulted in 14 subclones, designated SpESF-X1 through 14. FIG. 8 summarizes the growth properties and viability of the 14 SpESF-X subclones. AUCs were calculated for each subclone. Based on these data, 5 subclones were compared to the parental SpESF-X (before subcloning), Sp2/0, and SpEEE cell lines (FIG. 9). SpESF-X2 survived for a longer period of time than the other subclones and had the highest AUC. By comparison, SpESF-X6 reached a higher density than any other subclone, but had the lowest AUC. To further select the best X clone as the host cells, transfection may need to be performed with each subclone to determine if or how the improved growth characteristics of each clone will actually translate into increased protein expression. Additional examples of recombinant proteins expressed in SpESF or SpESF-X are listed in Table 6.

TABLE 6

Recombinant proteins expressed in SpESF or SpESF-X

| Construct | Antigen | Structure | Host Cell Line |
|---|---|---|---|
| C-DDD2-Fab-hMN-14 | CEACAM5 | $(Fab)_2$ | SpESF |
| hA20-Fab-DDD2 | CD20 | $(Fab)_2$ | SpESF |
| h679-Fab-AD2 | HSG | Fab | SpESF and SpESF-X |
| hL243-IgG | HLA-DR | IgG | SpESF |
| hL243-IgG-AD2 | HLA-DR | IgG | SpESF and SpESF-X |
| hA19-Fab-DDD2 | CD19 | $(Fab)_2$ | SpESF-X |
| hR1-IgG-AD2 | IGF1R | IgG | SpESF and SpESF-X |
| hPAM4-Fab-DDD2 | Muc1 | $(Fab)_2$ | SpESF |
| hL243-Fab-DDD1 | HLA-DR | $(Fab)_2$ | SpESF-X |
| hL243-Fab-DDD2 | HLA-DR | $(Fab)_2$ | SpESF-X |
| CDDD2-Fab-hRS7 | EGP-1 | $(Fab)_2$ | SpESF-X |
| hMN-15-Fab-DDD2 | CEACAM6 | $(Fab)_2$ | SpESF |
| Epo-DDD2 | N/A | N/A | SpESF |
| hR1-Fab-DDD2 | IGF1R | $(Fab)_2$ | SpESF |
| hA20-IgG-AD2 | CD20 | IgG | SpESF |
| hLL2-IgG-AD2 | CD22 | IgG | SpESF |
| hLL1-Fab-DDD2 | CD74 | $(Fab)_2$ | SpESF |

Conclusions

Bcl-2 is a pro-survival/anti-apoptotic protein. It has been demonstrated by several groups that a Bcl-2 deletion mutant missing the flexible loop domain (FLD) has an enhanced ability to inhibit apoptosis (Figueroa et al., 2001; Chang et al., 1997). More recently, it was demonstrated that mutation of 1 to 3 serine/threonine residues in the FLD of Bcl-2 to glutamic acid, which mimics hyper-phosphorylation, significantly enhances its anti-apoptotic ability (Deng et al., 2004). Phosphorylation at these or other residues in the positive regulatory domain (aa 69-87) of the FLD appears to block binding of p53 to the negative regulatory domain (aa 32-68) and functions to maintain Bcl-2's survival function (Deng et al., 2006, Mol Cell Biol 26(12):4421-4434).

We have generated three murine myeloma host cell lines, which carry the BCL-2 triple mutant (T69E, S70E and S87E), for the expression of recombinant proteins. The transfection efficiency of the hBCL2(EEE)-pZeoSV2+ vector was very high for SP2/0 cells. A total of 40 wells were chosen randomly from the plates with the highest zeocin concentration and analyzed by anti-Bcl-2 immunoblot. A wide range of expression levels was observed and the cells with the highest Bcl-2-EEE were immediately sub-cloned by limiting dilution.

Over-expression of Bcl-2-EEE appears to inhibit apoptosis in SP2/0 cells. This effect was largely dose-dependent, since clones with higher expression levels had a tendency to survive longer than those with lower levels. Bcl-2 expression was not detected in untransfected SP2/0 cells. The highest Bcl-2-EEE-expressing clone grew to a 15-20% higher cell density and survived an additional 4-6 days in batch culture compared to SP2/0 cells.

Serum-deprivation experiments demonstrated that SpEEE clone #87-29 (SpESF) possessed enhanced survival function, presumably due to its resistance to apoptosis. This property allowed the facile adaptation to growth in serum-free media and eliminated the requirement of serum over the entire cell line development process, including transfection, gene amplification, subcloning, and cryopreservation. This and other qualities make these attractive host cell lines for recombinant protein expression. Expression of Bcl-2-EEE, which is stable in the absence of zeocin selection, has resulted in the generation of a robust cell line that reaches high cell-density and sustains high cell viability for an extended period of time. The absence of serum reduces many potential risks associated with the use of animal products, such as the introduction of adventitious agents (Merten, 1999, Dev Biol Stand 99:167-180). And finally, the development of stable recombinant protein-expressing cell lines is expedited because no additional serum-weaning step is required. Both SpESF and SpESF-X have been shown to be suitable host cells for generating mAb-production cell lines from transfection to expression, all in serum-free medium, reaching $4\times10^6$ cells/ml and yielding 150 to 200 mg/mL in batch cultures.

The PERC.6 and NSO-PFCF are two promising serum-free cell line platforms for monoclonal antibody production; however, they both require supplementation with 10% FBS during transfection to help the cells recover (Jones, et al., 2003; Hartman, et al., 2006, Biotechnol Bioeng 96:294-306). In addition, several serum-free cell lines exist that have been used for large-scale, transient transfection of recombinant proteins (Rosser, et al., 2005; Pham, et al., 2003, Biotechnol Bioeng 84:332-342; Derouazi, et al., 2004, Biotech Bioeng. 87(4):537-545). As far as the inventors are aware, this is the first successful application of a serum-free cell line for the stable production of recombinant proteins.

Example 14

Production of Human Growth Hormone in SpESF-X Cells

A cDNA encoding human growth hormone (e.g, GenBank Accession No. NM 000515) is cloned into a mammalian expression vector and transfected into SpESF-X cells by electroporation as disclosed in Example 12. Cells are plated into 96-well plates and selected with 0.15 KM MTX. Production of hGH is confirmed by immunoassay using antibody against hGH. High-level producing clones of hGH are selected and subcloned by limiting dilution. Several subcloned cell lines are maintained in cell culture. The SpESF-X cells are stably transfected with the hGH expression vector and produce hGH at a level of over 150 mg protein/mL of growth medium.

What is claimed is:

1. A method of protein production comprising:

a) obtaining a cell line comprising a gene encoding a mutant Bcl-2 protein, said protein comprising T69E, S70E and S87E amino acid substitutions;

b) adapting said cell line to grow in serum-free medium to produce a pre-adapted cell line; and c) transfecting said pre-adapted cell line under serum-free conditions with one or more expression vectors expressing a protein of interest.

2. The method of claim 1, said transfected cell line is capable of producing the protein of interest without further adaptation to serum free conditions.

3. The method of claim 1, wherein the expression vector encodes an antibody, humanized antibody, chimeric antibody, human antibody, bispecific antibody, multispecific antibody, multivalent antibody or fragment thereof.

4. The method of claim 1, wherein the cell line is not a CHO cell line.

5. The method of claim 1, further comprising freezing the pre-adapted cell line for storage prior to transfection with one or more expression vectors expressing a protein of interest.

6. The method of claim 1, wherein the expression vector encodes a growth factor, hormone, cytokine, chemokine, interleukin, interferon, an enzyme, a peptide, a vaccine, EPO, G-CSF, GM-CSF, EGF, VEGF, thrombopoietin, IL-1 through IL-31, interferon-alpha, interferon-beta or interferon-gamma.

7. The method of claim 1, wherein the transfected cell line produces the protein of interest at a yield of at least 150 mg protein/mL of growth medium.

8. The method of claim 1, further comprising adding one or more growth factors, cytokines or hormones to the medium.

9. The method of claim 8, wherein the growth factor, cytokine or hormone is selected from the group consisting of erythropoietin, thrombopoietin, IL-2, IL-3, IL-4, IL-5, IL-6, IL-9, IL-11, IL-12, IL-13, IL-15, prolactin, growth hormone, G-CSF and GM-CSF.

10. The method of claim 1, further comprising exposing the cell line to methotrexate to amplify one or more nucleic acid sequences in the cell line.

11. The method of claim 10, further comprising growing the cell line under conditions that comprise overgrowth of the cells to a viability of 50 to 75%.

12. The method of claim 11, further comprising allowing the cells to recover in fresh medium.

13. The method of claim 12, further comprising repeating the overgrowth and recovery of the cell line.

* * * * *